(12) United States Patent
Toya et al.

(10) Patent No.: US 6,961,516 B2
(45) Date of Patent: Nov. 1, 2005

(54) STEAM GENERATOR AND MIXER USING THE SAME

(75) Inventors: Eiichi Toya, Tokyo (JP); Tomio Konn, Yamagata (JP)

(73) Assignee: Toshiba Ceramics Co., Ltd., Tokyo (JP)

( * ) Notice: Subject to any disclaimer, the term of this patent is extended or adjusted under 35 U.S.C. 154(b) by 10 days.

(21) Appl. No.: 10/811,822

(22) Filed: Mar. 30, 2004

(65) Prior Publication Data

US 2004/0247302 A1 Dec. 9, 2004

(30) Foreign Application Priority Data

Mar. 31, 2003 (JP) ........................................ 2003-093688
Mar. 31, 2003 (JP) ........................................ 2003-093689

(51) Int. Cl.[7] ............................................... F22B 29/06
(52) U.S. Cl. ....................................... 392/397; 392/405
(58) Field of Search ................................. 392/386, 394, 392/396, 399, 400, 401, 402, 403, 404, 405, 406; 219/544, 546, 547, 548, 549

(56) References Cited

U.S. PATENT DOCUMENTS

| | | | |
|---|---|---|---|
| 3,472,455 A | 10/1969 | Johnson et al. | |
| 4,430,994 A | 2/1984 | Clawson et al. | |
| 4,682,010 A | 7/1987 | Drapeau et al. | |
| 5,195,515 A | * 3/1993 | Levine | 128/203.26 |
| 5,943,473 A | * 8/1999 | Levine | 392/401 |
| 6,031,968 A | 2/2000 | Holtmann | |
| 6,043,468 A | * 3/2000 | Toya et al. | 219/544 |
| 6,102,037 A | 8/2000 | Koch | |

FOREIGN PATENT DOCUMENTS

| | | |
|---|---|---|
| EP | 0 125 210 A1 | 11/1984 |
| FR | 2 565 827 A1 | 12/1985 |
| JP | 5-272331 A | 10/1993 |
| JP | 2000-126296 A | 5/2000 |
| WO | WO 03/043560 A2 | 5/2003 |
| WO | WO 03/055555 A1 | 7/2003 |

* cited by examiner

Primary Examiner—Sang Paik
(74) Attorney, Agent, or Firm—Foley & Lardner LLP

(57) ABSTRACT

A steam generating apparatus includes: a liquid tank portion 1 for storing a liquid; an evaporator portion 2 which is directly connected to the liquid tank portion, heats the liquid supplied from the liquid tank portion, and generates steam; a steam storage portion 3 which is directly connected to the evaporator portion, and stores the steam generated by the evaporator portion; a passageway 4 which is directly connected to the steam storage portion and outwardly passes the generated steam; a liquid pathway 10b which is connected to the liquid tank portion, and supplies the liquid; and a heater unit 20 which is provided on one side of the evaporator portion, and heats at least the evaporator portion. The liquid tank portion 1, the evaporator portion 2, the steam storage portion 3, the passageway 4, and the liquid pathway 10b are formed within an integral member of a translucent material.

19 Claims, 24 Drawing Sheets

STEAM GENERATOR AND MIXER USING THE SAME

BACKGROUND OF THE INVENTION

1. Field of the Invention

The present invention relates to a steam generator, more particularly to a steam generator capable of generating steam in a short period of time. Further, the present invention relates to a mixer using the above-mentioned steam generator, more particularly to a mixer which generates a mixed gas by mixing steam with another material.

2. Description of the Related Art

A steam generating apparatus is used for a steam type inhaler which sucks up and sprays a liquid by means of using discharge of steam, an exhaust gas purifying apparatus as will be described later, etc., for example.

Firstly, the steam generating apparatus used for the steam type inhaler will be described. In this type of steam type inhaler, a nozzle which discharges the steam is provided and an upper end of a sucking tube whose other end is put in a liquid within a liquid tank is disposed in the vicinity of the above-mentioned nozzle. Water is heated to generate steam. When the steam is discharged through the nozzle, a liquid will be sucked up through the sucking tube and atomized along a steam flow as the steam is discharged.

In this case, in order to shorten a time period between start of heating and start of atomizing after the steam is generated, the water in a feed water tank is not directly heated, but a heat chamber of small capacity is provided separately, and part of water in the feed water tank is led to the heat chamber in which steam is generated.

For more detailed description, an example will be described. For example, a steam suction apparatus proposed in Japanese Laid Open Patent No. 2000-126296 will be described with reference to FIG. 34.

Reference numeral 101 in the figure depicts a feed water tank portion. Reference numeral 103 denotes a heat chamber provided with a heater 102 on its wall surface. A bottom part of a feed liquid tank portion 101 and a bottom part of a heat chamber 103 are communicated with each other through a conductive tube passage 104. An upper space of the heat chamber 103 and an upper space of the feed liquid tank portion 101 are communicated with each other through a steam passage hole (not shown). The steam which is generated in the heat chamber 103 and flowed into the upper space of the feed liquid tank portion 101 is adapted to be directed to a nozzle 105.

In addition, reference numeral 106 in the figure denotes a sucking tube, one end of which is disposed in the liquid tank; reference numeral 107 depicts a relief valve which opens when a steam pressure in the feed liquid tank portion 101 increases, so as to release the pressure; reference numeral 108 indicates a lid which closes an upper end opening of the feed liquid tank portion 101.

In this steam suction apparatus, water is supplied from the feed liquid tank portion 101 to the heating unit 103; the steam generated in this heating unit 103 flows into the upper space of the feed liquid tank portion 101. Then, the above-mentioned steam is supplied from the upper space of the feed liquid tank portion 101 to the nozzle 105, and is discharged through the nozzle 105. In this way the upper end of the sucking tube 106 is caused to have a negative pressure, so that the liquid is sucked up through the sucking tube 106 and is atomized along the steam flow.

A disadvantage of such an apparatus is that the steam generating apparatus used for the steam suction apparatus is generally made of metal, such as iron and aluminum and heat from the heater 102 escapes to a body (casing) of the apparatus, so that the water in the heating unit 103 cannot be heated effectively, the thermal efficiency is low, and it is not possible to perform rapid heating. The document does not disclose how to solve a problem that the time between the start of heating and the start of atomizing after the steam is generated.

Moreover, the heater 102 is arranged on a wall surface of the heat chamber 103 in the above-mentioned steam generating apparatus so that the water may be heated directly. Therefore, in order to prevent leakage, it is necessary to provide a member, such as an 0 ring 109, between the heater 102 and the wall surface, and to maintain the member according to used hours.

Furthermore, in the above-mentioned steam generating apparatus, the feed liquid tank portion 101 and the heat chamber 103 are connected by pipes, the upper space of the heat chamber 103 and the upper space of the feed water tank are communicated with each other through the steam passage hole, and the feed liquid tank portion 101 and the nozzle are connected by a pipe. Thus, there is a problem that the whole apparatus is complicated and its manufacturing costs increase.

The steam generating apparatus is used also in an exhaust gas purifying apparatus. Now, we describe an example of this exhaust gas purifying apparatus. For example, in Japanese Laid Open Patent No. H05-272331, as shown in FIG. 35, an exhaust gas purifying apparatus is disclosed which comprises an $NO_x$ reduction catalyst 151 disposed in the middle of an exhaust pipe of a diesel engine 150, a reducing agent feed nozzle 154 disposed on an upstream side of the $NO_x$ reduction catalyst 151 of an exhaust pipe 153, a reduction gas generator 155 connected to the reducing agent feed nozzle 154, a urea supply device 157 which supplies solid urea 156 to the reduction gas generator 155, and an air supply device 158 which supplies air to the reduction gas generator 155.

This exhaust gas purifying apparatus thermally decomposes the solid urea 156 whilst being supplied with air, so as to generate a reduction gas which is supplied to an exhaust gas channel upstream of the $NO_x$ reduction catalyst 151.

In other words, the above-mentioned reduction gas generator 155 is equivalent to the above-mentioned steam generator, and is a mixer in terms of mixing the reduction gas with air.

Now, describing it more particularly, the above-mentioned reduction gas generator 155 comprises an outer casing 159, an air inlet 160 and a reduction gas outlet 161, a flue 162 concentrically arranged within the outer casing 159, and an electric heater 163 arranged around this flue 162.

In addition, the urea supply device 157 comprises a tank 164 and a screw feeder 165. This tank 164 is manufactured to be of a "hopper" type, at an upper end of which an inlet 166 is provided, and at a lower end of which an outlet 167 is provided. The tank 164 is filled with the solid urea 156 which is ground in advance. Moreover, the above-mentioned screw feeder 165 comprises a screw case 168, a screw 169 disposed in the above-mentioned screw case 168, and a motor 170. Furthermore, the above-mentioned air supply apparatus 158 comprises an air tank 172 connected to the air inlet 160 of the flue 162 by means of piping 171, and an air compressor (not shown) connected to the air tank 172.

In the thus constituted reduction gas (thermal decomposition gas) generating apparatus, a screw 169 is rotated and the powdery solid urea 156 is supplied from a tank 164 into the flue 162. On the other hand, while the inside of the above-mentioned flue 162 is heated by the electric heater 163, air is supplied from the air tank 172.

As a result, the solid urea 156 is thermally decomposed so as to be a reduction gas, which is conveyed to the reducing agent feed nozzle 154 by means of the supplied air.

A reduction gas generator (mixer) used for the above-mentioned purifying apparatus is constructed such that the solid urea is supplied to the inside of the flue so a to be heated inside the flue. Therefore, there is a technical problem that the solid urea should be rapidly heated inside the flue, so that a large-sized heater should be used.

Moreover, the air supply device is used for generating and conveying the above-mentioned thermal decomposition gas (reduction gas), however, there is another technical problem that a temperature in the flue is decreased by the air supply, so that the thermal efficiency is reduced.

Furthermore, the reduction gas generator (mixer) used for the above-mentioned purifying apparatus, the urea supply device, and the air supply device are each formed separately; the urea is adapted to be supplied by the screw feeder; and the air is adapted to be supplied from an air tank. Therefore, there is a technical problem that the whole apparatus becomes larger.

Furthermore, in the above-mentioned purifying apparatus, compressed air is used as a means to pump the reduction gas to an exhaust-gas passage, so that an apparatus, such as an air tank for storing the compressed, a compressor, etc. is needed. Thus, there is another technical problem that the apparatus becomes larger and more complicated so that it is difficult to load it on a vehicle.

In addition, the flue etc. might corrode by ammonia generated when the solid urea is thermally decomposed. In order to solve this, it may be possible lo apply a Teflon (registered trademark) coating inside the flue. However, there is another technical problem that the application of the coating may be labor intensive and expensive.

SUMMARY OF THE INVENTION

The present invention is made in order to solve the above-mentioned technical problems, an aim of the present invention is to provide a steam generator which is capable of supplying steam stably and efficiently, moreover, generating steam in a short period of time, for ease of construction and ease of maintenance.

Another aim of the present invention is to provide a mixer which is small, and whose thermal efficiency is good, can generate a mixed gas (including a thermal decomposition gas) efficiently, and has an advantage in corrosion resistance by using the above-mentioned steam generator.

The present invention has been made in order to solve the above-mentioned technical problems, and a steam generating apparatus in accordance with the present invention is characterized by comprising: a liquid tank portion for storing a liquid, an evaporator portion which is directly connected to the above-mentioned liquid tank portion, heats the liquid supplied from the above-mentioned liquid tank portion, and generates steam, a steam storage portion which is directly connected to the above-mentioned evaporator portion, and stores the steam generated by the above-mentioned evaporator portion, a passageway which is directly connected to the above-mentioned steam storage portion and outwardly passes the steam generated by the above-mentioned evaporator portion, a liquid pathway which is connected to the above-mentioned liquid tank portion, and supplies the liquid to the above-mentioned liquid tank portion, and a heater unit which is provided on one side of the above-mentioned evaporator portion, and heats at least the evaporator portion, wherein the above-mentioned liquid tank portion, the evaporator portion, the steam storage portion, the passageway, and the liquid pathway are formed within an integral member of a translucent material In the steam generator in accordance with the present invention, the above-mentioned liquid tank, the evaporator portion, the steam storage portion, the passageway, and the liquid pathway are formed within the integral member of the translucent material; the liquid tank and the evaporator portion are connected directly, without using a pipe (piping) etc.; and the evaporator portion and the steam storage portion are connected directly. As described above, since a pipe (piping) is not used, the whole apparatus can be simplified and its heat capacity can be made smaller.

As a result, even a small heater allows rapid heating. Further, it is possible to shorten the time period between the start of heating and the start of atomizing after the steam is generated.

It is desirable that the integral member formed of the above-mentioned translucent material is a glass body, and it is also desirable that the above-mentioned integral member is a transparent glass body, a transparent borosilicate glass body, or a transparent soda glass body. More preferably it is a transparent silica glass body.

As described above, when the integral member formed of the above-mentioned translucent material is made of the glass body, heat transfer by means of the heater unit and heating by radiant heat can be attained, thus improving thermal efficiency. Moreover, a glass body has a low heat capacity, and therefore its temperature can rapidly be increased or decreased, thus preventing damages etc. due to a rapid change in temperature.

Furthermore, it is excellent in corrosion resistance and may be manufactured inexpensively. It is desirable that, from a viewpoint of thermal efficiency, a transverse sectional area of the above-mentioned evaporator portion is smaller than a transverse sectional area of the liquid tank portion, and it is formed so that the transverse sectional area may gradually spread or expand from the liquid tank portion side towards the steam storage portion side.

Furthermore, in terms of smooth supplying of water to the evaporator portion and prevention of bumping, it is preferable to provide a porous body at the above-mentioned evaporator portion and in the liquid tank portion.

In addition, from a viewpoint of antioxidation, it is desirable that the above-mentioned porous body is provided in the water.

It is desirable that a vertical section of the above-mentioned passageway is formed into a trapezoid or a trapezium where the section spreads or expands gradually outwards, and a diffusion plate is provided in the above-mentioned passageway.

Moreover, it is desirable that the above-mentioned heater unit is a heater in which the carbon wire heater body is enclosed in a glass plate. In addition, since the carbon wire heater body is enclosed in the glass plate, oxidation of carbon can be prevented.

Furthermore, it is desirable that the above-mentioned heater unit encloses the carbon wire heater body in the glass plate by welding together a first glass plate in which a slot where the carbon wire heater body is accommodated is formed and a second glass plate which covers the above-mentioned slot.

By constituting the heater unit in this way, the carbon wire heater body can be easily enclosed in the glass plate.

In the steam generator according to the present invention, by providing the above mentioned heater unit at the above-mentioned glass body, a generator construction body other than the above-mentioned carbon wire heater body and/or the above-mentioned porous body can be made of glass only (single material) so that the temperature may be raised or reduced very rapidly. Moreover, the number of components can be reduced and it is possible to provide a robust steam generator.

As to the above-mentioned heater unit, since a wiring pattern of the above-mentioned carbon wire heater body can be changed considerably freely, it is possible to heat only a desired part partially or locally, by changing wiring density, the number of the carbon wire heater bodies, and a size thereof partially.

By providing the above-mentioned heater unit separately from the above-mentioned glass body, the above-mentioned glass body can be easily cleaned under severe conditions, such as by means of a highly concentrated chemical solution or empty heating, so that it becomes possible to mix the material and the steam at a constant high purity and under the same condition.

Furthermore, it is preferable to form the liquid tank portion, the evaporator portion, the steam storage portion, and the passageway as a recess at the above-mentioned glass body, to cover an opening side of the above-mentioned recess by the heater unit in which the carbon wire heater body is enclosed in the glass plate, to integrate the above-mentioned glass body with the heater unit by welding the glass plate of the heater unit at the side surface of the above-mentioned glass body, to thereby form the liquid tank portion, the evaporator portion, a steam storage portion, and the passageway.

As described above, since every part, such as the liquid tank portion etc., is formed as the recess, every part can be easily formed at the glass body. When the respective parts are formed separately, connecting pipes which mutually connect the respective necessary parts of the separate bodies or various fixtures for connecting them are unnecessary. Further, by integrating the above-mentioned glass body with the glass plate of the heater unit by welding, the steam generator can be simpler and smaller.

Furthermore, it is desirable that the glass body in which at least the above-mentioned liquid tank portion, the evaporator portion, the steam storage portion, and the passageway are formed and the heater unit provided on the side of the above-mentioned glass body are surrounded by a thermal insulation material, and contained in a metal casing. Since the respective parts are constructed in this way, it is possible to improve the thermal efficiency and prevent damages etc.

The present invention is made in order to solve the above-mentioned technical problems.

A mixer in accordance with the present invention is a mixer using a steam generator which comprises: a liquid tank portion for storing a liquid; an evaporator portion which is directly connected to the above-mentioned liquid tank portion, heats the liquid supplied from the above-mentioned liquid tank portion, and generates steam; a steam storage portion which is directly connected to the above-mentioned evaporator portion, and stores the steam generated by the above-mentioned evaporator portion; and a liquid pathway which is connected to the above-mentioned liquid tank portion, and supplies the liquid to the above-mentioned liquid tank portion, wherein the above-mentioned liquid tank portion, the evaporator portion, the steam storage portion, and the liquid pathway are formed in a silica glass body, wherein a material heating unit for heating the above-mentioned material, a mixing portion for mixing the steam from the above-mentioned steam storage portion and the material so as to generate a mixed gas, and a passageway which passes the above-mentioned mixed gas outside are formed; and a heater unit for heating the above-mentioned evaporator portion and the material heating unit is provided on a side of the above-mentioned silica glass body.

According to the present invention, the mixer has the heating function of the above-mentioned heater unit; and the function of deriving the mixed gas, via a derivation portion, the mixed gas being obtained such that, by means of the silica glass body which integrally has the above-mentioned liquid tank portion, the evaporator portion, the steam storage portion, the material heating unit, the mixing portion, and the mixed gas passageway, either the material which comprises the liquid or the solid is heated in the material heating unit, the liquid material is heated, or the solid material is heated and liquefied, then the resulting material is mixed with the steam which is generated by heating, in the evaporator portion, the liquid stored in the liquid tank portion so as to obtain the mixture gas at the mixing portion, whereby it is possible to provide the small mixer allowing excellent corrosion resistance and the improved thermal efficiency.

In addition, the above-mentioned mixed gas may be a mixed gas including a material and steam, or a mixed gas including a gas thermally decomposed from a material by steam.

It is desirable to have the liquid tank for storing water as the above-mentioned liquid and the steam storage portion for communicating with the above-mentioned evaporator portion and for storing the steam generated by the above-mentioned evaporator portion, to mix the steam and the material from the above-mentioned steam storage portion in the above-mentioned mixing portion, and to generate the mixed gas.

It is also desirable to have the steam storage portion for communicating with the above-mentioned evaporator portion and for storing the steam generated by the above-mentioned evaporator portion, the steam supplying passage extending from the above-mentioned steam storage portion to the mixing portion, and the steam supply passage extending from the above-mentioned steam storage portion lo the material heating unit, to supply the steam to the above-mentioned material heating unit, to mix the steam and the material from the above-mentioned steam storage portion, and to generate the mixed gas in the above-mentioned mixing portion.

As described above, since a part of steam stored in the steam storage portion is adapted to be supplied to the above-mentioned material heating unit, viscosity of the material can be reduced and fluidity of the material can be improved. As a result, dispersibility of the material in the mixing portion is improved, and the more uniform mixture with steam is promoted.

Furthermore, it is desirable to arrange the porous body in the steam supply passage extended from the above-mentioned steam storage portion to the material heating unit.

In this way the porous body is arranged in the steam supply passage, so that it is possible to prevent the material from entering the steam supply passage. Moreover, it is possible to improve a dispersion effect of the steam dispersing into the material in the material heating unit, so that the material may have a uniform viscosity.

It is desirable to provide a material container portion for containing the material within the above-mentioned silica glass body, and to provide the material heating unit for heating the material at the lower part of the above-mentioned material container portion. Thus, it is possible to supply the material to the mixing portion more smoothly.

It is desirable that the above-mentioned steam supply passage is connected to the material supply passage at an angle of 0 degree to 45 degrees therebetween, at an interconnection between the steam supply passage connected from the above-mentioned steam storage portion to the mixing portion and the material supply passage extended from the above-mentioned material heating unit to the mixing portion.

Having this angle, it is possible to provide a sufficient effect of sucking the material by supplying the above-mentioned steam, so that thorough mixing in the mixing portion can be performed.

In addition, it is more preferable that the interconnection between the steam supply passage extending from the above-mentioned steam storage portion to the mixing portion and the material supply passage extending from the above-mentioned material heating unit to the mixing portion is formed into a double tube structure in which the above-mentioned steam supply passage covers a periphery of the material supply passage. In this case, both are connected at an angle of 0 degree.

Thus, an effect of sucking the material by means of the above-mentioned steam supply increases more greatly, so that it is possible to mix the steam and the material or to mix them accompanied by thermal decomposition more effectively.

Preferably, the above-mentioned heater unit is a heater in which the carbon wire heater body is enclosed in the silica glass plate; the liquid tank portion, the evaporator portion, the steam storage portion, the material heating unit, the mixing portion, and the passageway are formed as a recess at the silica glass body; and the opening side of the above-mentioned recess is covered by welding the silica glass plate of the above-mentioned heater unit to the above-mentioned silica glass body, whereby a water tank portion, the evaporator portion, the steam storage portion, the material container portion, the material heating unit, the mixing portion, and the passageway are formed.

The above-mentioned heater unit is the heater in which the carbon wire heater is enclosed in the silica glass plate, and therefore can prevent carbon from being oxidized.

By providing such a heater unit at the above-mentioned silica glass body, a mixer construction body other than the above-mentioned carbon wire heater body and/or the above-mentioned porous body can consist of silica glass only (single material), so that the temperature can be raised or reduced very rapidly. Further, the number of parts can be reduced and it is possible to provide a robust mixer.

As to the above-mentioned heater unit, since the wiring pattern of the above-mentioned carbon wire heater body can be changed considerably freely, it is possible to heat only a desired part partially or locally, by changing wiring density, the number of the carbon wire heater bodies, and the size thereof partially.

By providing the above-mentioned heater unit separately from the above-mentioned silica glass body, the above-mentioned silica glass body can be easily cleaned under severe conditions, such as by means of the highly concentrated chemical solution or empty heating, so that it becomes possible to mix the material and the steam at the constant high purity and under the same condition.

Furthermore, since every part, such as the liquid tank portion, is formed as the recess, every part can be easily formed at the silica glass body. When respective parts are formed separately, connecting pipes which mutually connect the respective necessary parts of the separate bodies or various fixtures for connecting them are unnecessary. By integrating the silica glass body with the above-mentioned silica glass plate of the above-mentioned heater unit by means welding, the mixer can be simpler and smaller.

Preferably, the carbon wire heater body of the above-mentioned heater unit is arranged to be located at least on sides of or in the vicinity of the above-mentioned evaporator portion, the steam storage portion, and the material heating unit. The carbon wire heater body is disposed at least on the sides of or the in the vicinity of the above-mentioned three members, so that generation of the mixed gas can be controlled more efficiently and more precisely.

It is desirable that the silica glass body at which at least the above-mentioned liquid tank portion, the evaporator portion, the material heating unit, the mixing portion, and the passageway are formed and the heater unit provided on the side of the above-mentioned silica glass body are surrounded by the thermal insulation material, and accommodated in the metal casing.

Because of the structure as described above, it is possible to improve the thermal efficiency and prevent damages etc.

Furthermore, it is desirable that the above-mentioned material is solid urea, the above-mentioned mixed gas is a gas including ammonia (a thermal decomposition gas), which can suitably be used for a mixer in the exhaust gas apparatus.

BRIEF DESCRIPTION OF THE DRAWINGS

FIGS. 3 are views of a heater unit as shown in FIG. 1.

FIG. 12 show a second embodiment of the steam generator in accordance with the present invention.

FIG. 17 show a sixth embodiment of the steam generator.

FIG. 18 show a seventh embodiment of the steam generator in accordance with the present invention.

FIG. 20 show a ninth embodiment of the steam generator.

FIG. 23 illustrate the heater unit as shown in FIG. 21.

FIG. 28B is a vertical sectional view.

DESCRIPTION OF THE PREFERRED EMBODIMENTS

Figure 1:
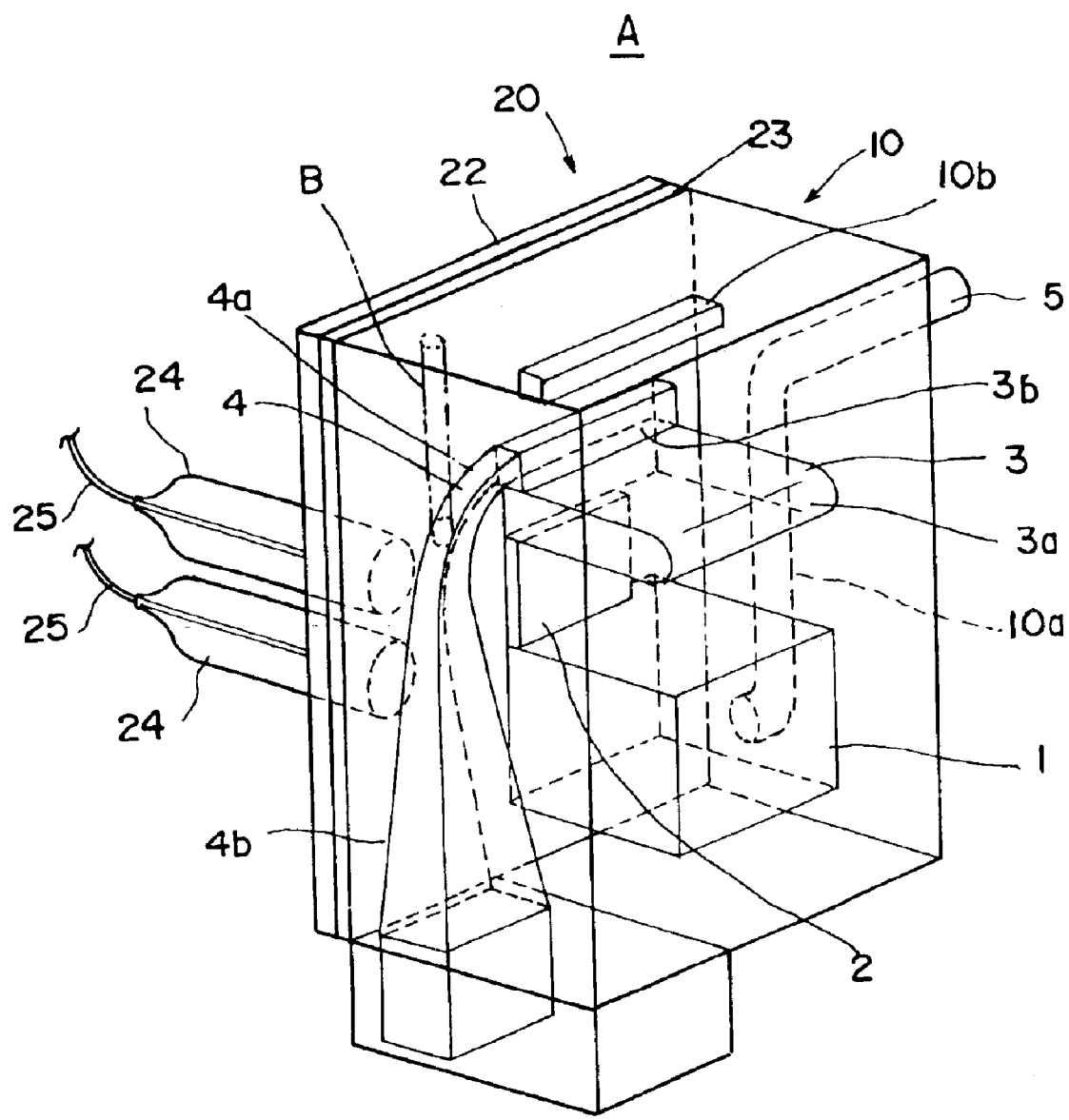
FIG. 1 is a perspective view showing a first embodiment of a steam generator in accordance with the present invention.
Figure 2:
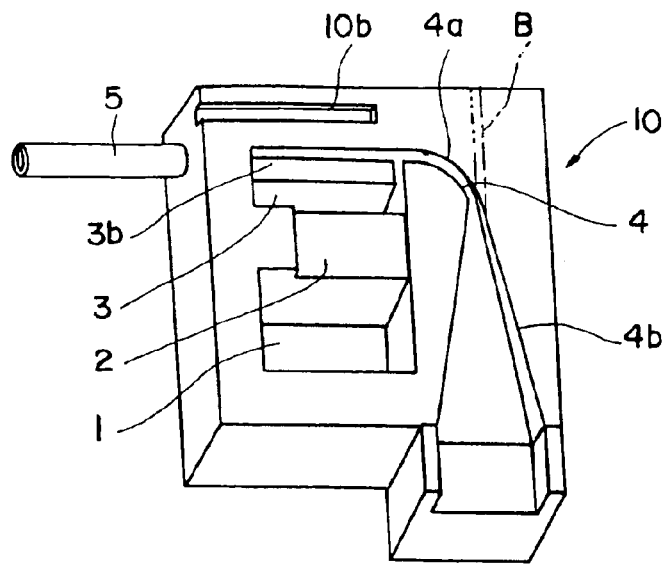
FIG. 2 is a perspective view of a glass body as shown in FIG. 1.
Figure 3A:
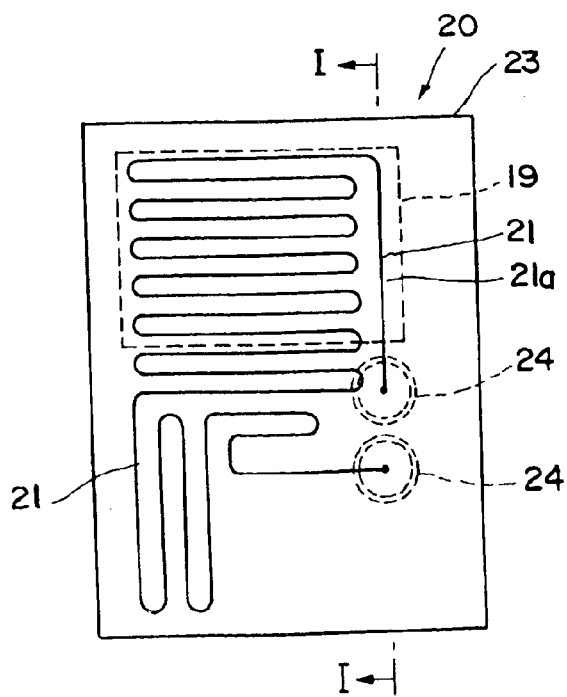
FIG. 3A is a view from a heater forming side.
Figure 3B:
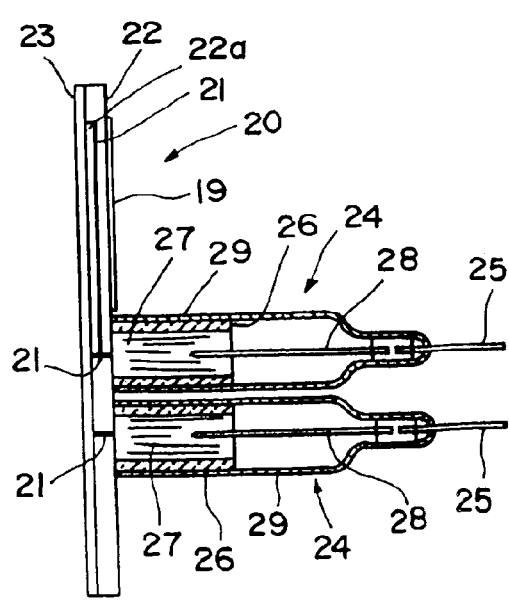
FIG. 3B is a cross-sectional view along the line I—I in FIG. 3A.
Figure 4:
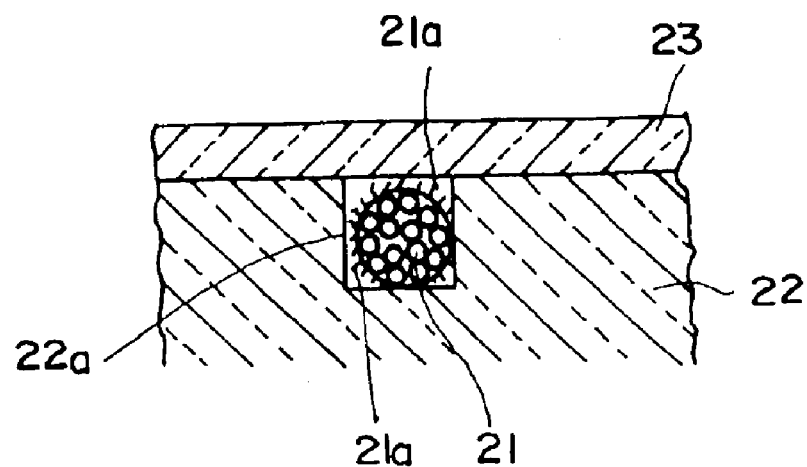
FIG. 4 is a cross-sectional view of the main part of the heater unit.
Figure 5:
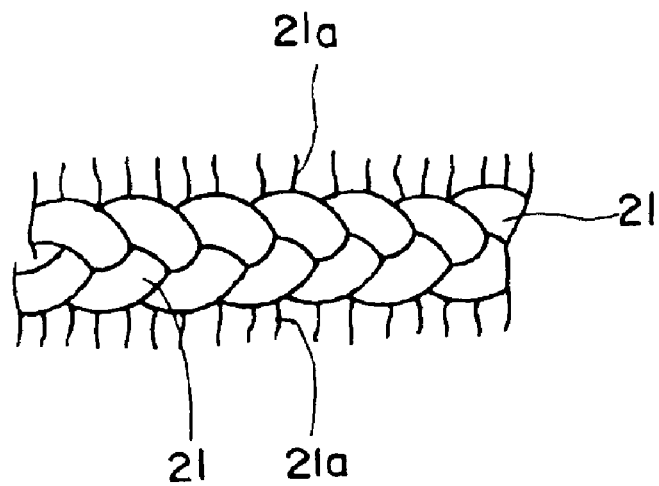
FIG. 5 is a view showing a carbon wire heater body.
Figure 6:
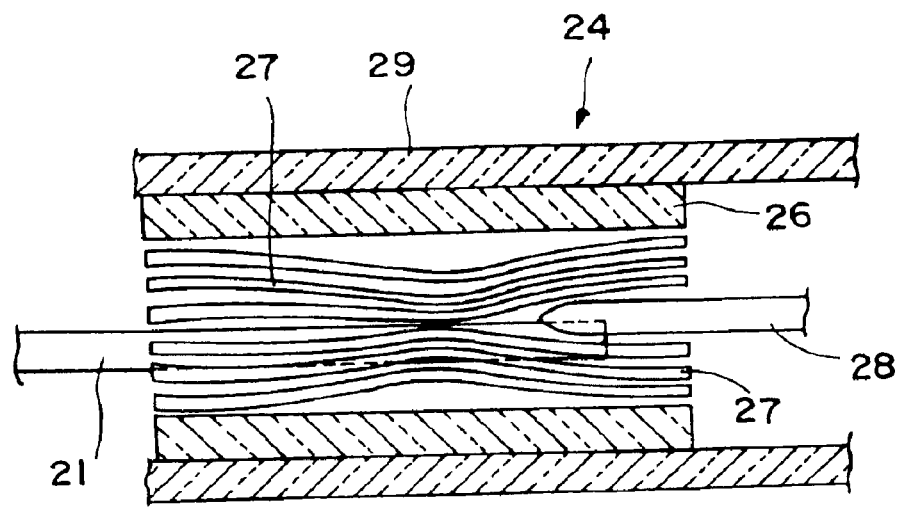
FIG. 6 is cross-sectional view of the main part of a sealing terminal portion of the heater unit.
Figure 7:
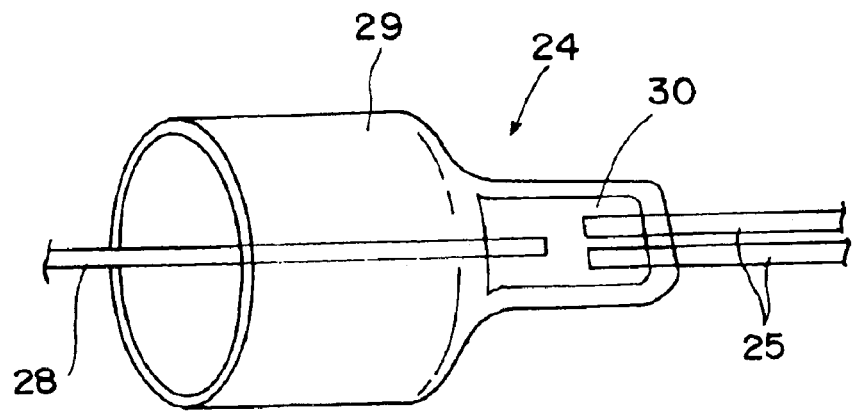
FIG. 7 is a perspective view showing a state of pinch seal of the sealing terminal portion of the heater unit.
Figure 8:
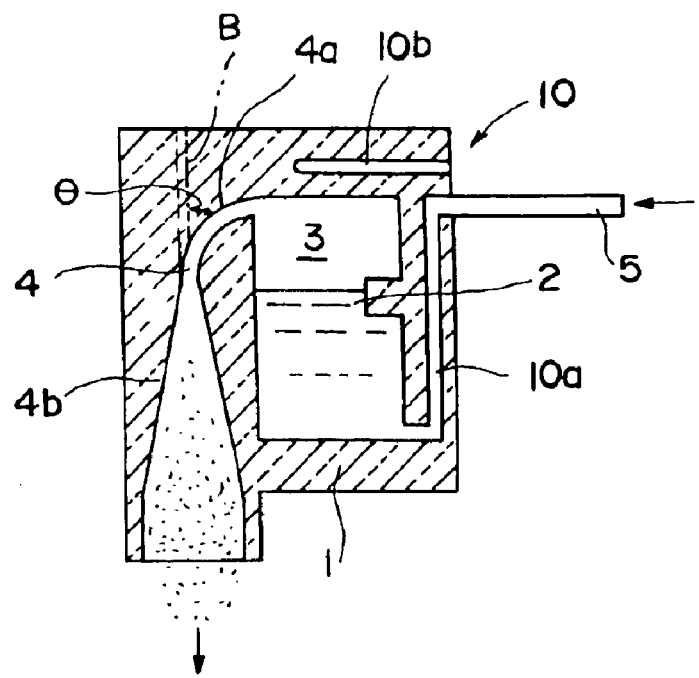
FIG. 8 is a schematic vertical sectional view of an embodiment as shown in FIG. 1.
Figure 9A:
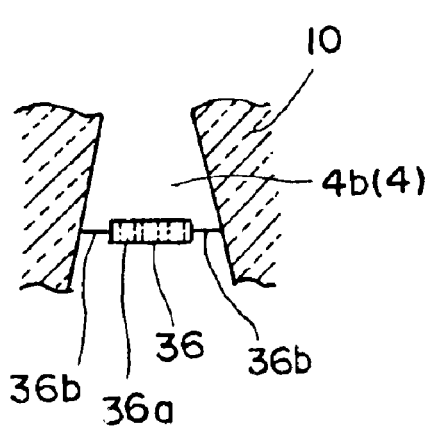
FIGS. 9A and 9B show a diffusion plate, and are respectively a front view and a side view.
Figure 9B:
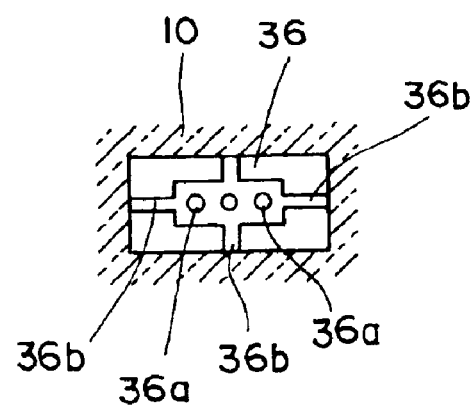
Figure 10:
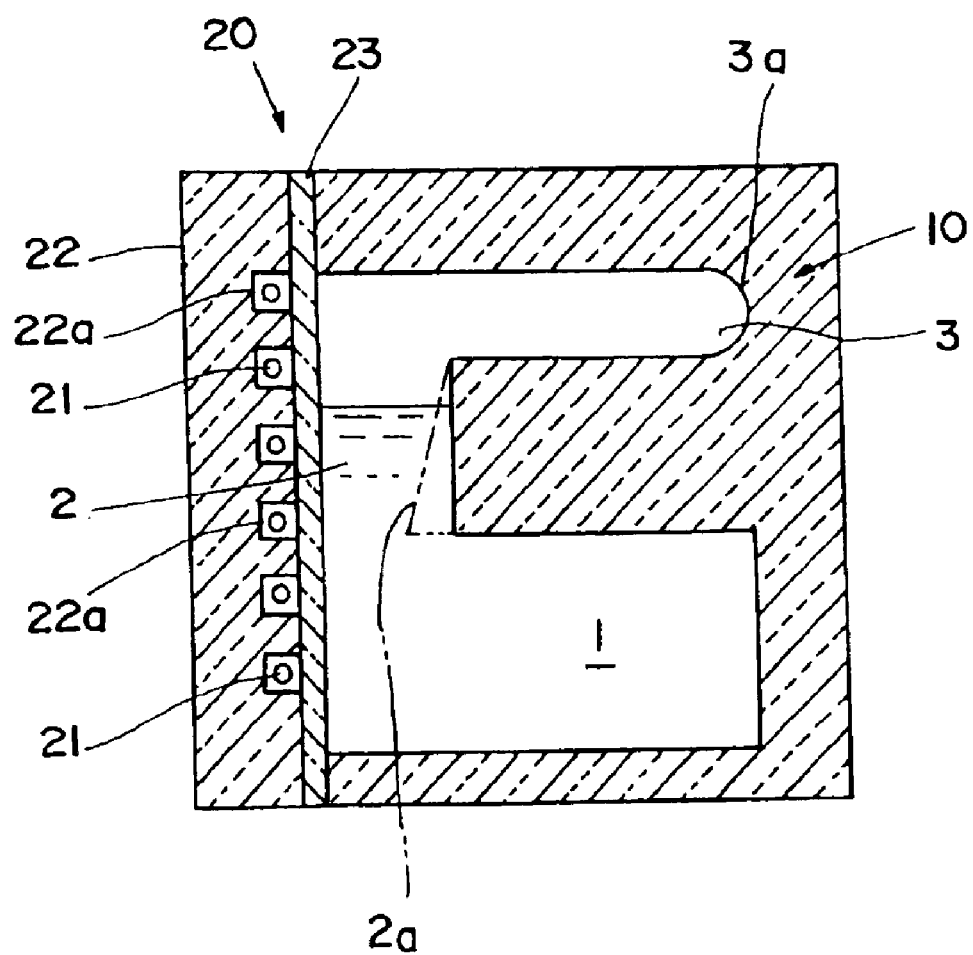
FIG. 10 is a schematic, vertical sectional view showing a modification of an evaporator portion in the first embodiment as shown in FIG. 1.
Figure 11:
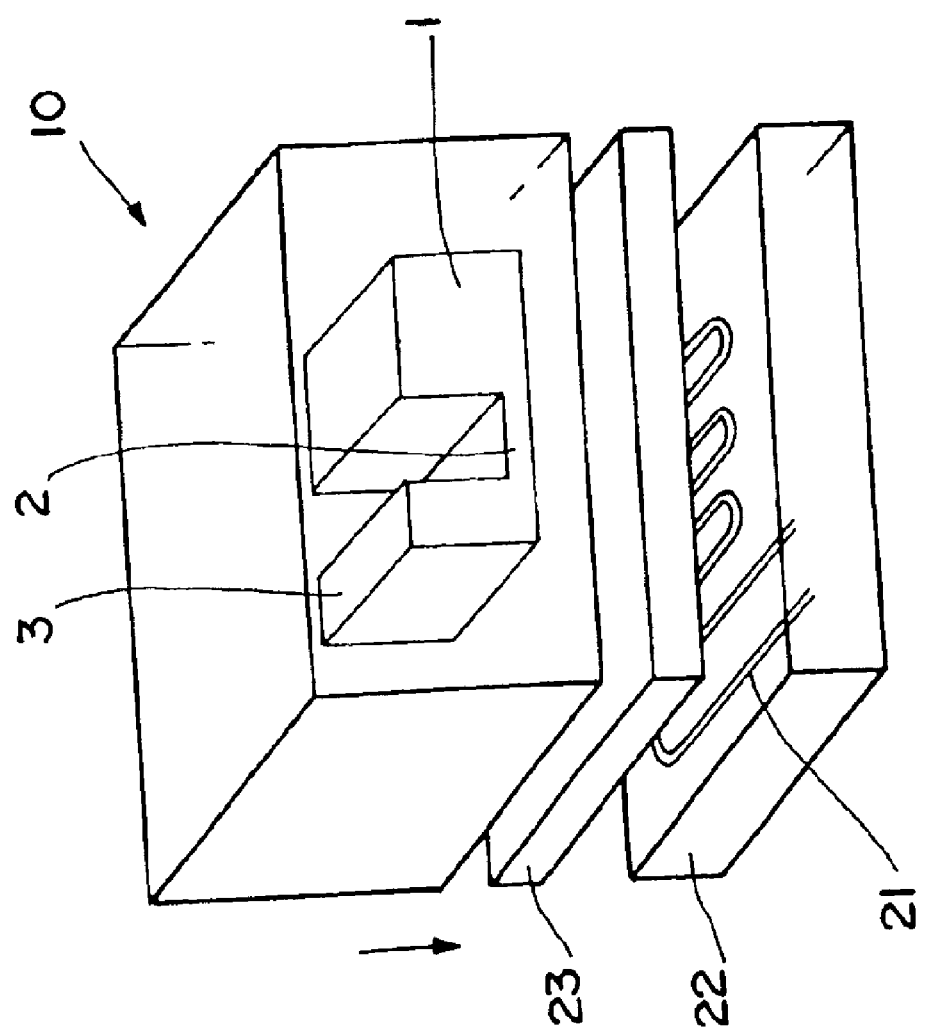
FIG. 11 is a schematic perspective view showing a method of manufacturing the steam generator of the first embodiment.

A first embodiment of a steam generating apparatus in accordance with the invention will be described with reference to FIG. 1 to FIG. 11. In addition, FIG. 1 is a perspective view showing a first embodiment of a steam generating apparatus in accordance with the present invention, FIG. 2 is a perspective view of a glass body as shown in FIG. 1, FIG. 3 are views of a heater unit as shown in FIG. 1, FIG. 3A is a view from a heater forming side, and FIG. 3B is a cross-sectional view along the line I—I. FIG. 4 is a cross-sectional view of the main part of the heater unit, FIG. 5 is a view showing a carbon wire heater body, FIG. 6 is a cross-sectional view of the main part of a sealing terminal portion of the heater unit, FIG. 7 is a perspective view showing a state of pinch seal of the sealing terminal portion of the heater unit. Furthermore, FIG. 8 is a schematic vertical sectional view of the embodiment as shown in FIG. 1, FIGS. 9A and 9B show a diffusion plate and are respectively a front view and a side view, FIG. 10 is a schematic vertical sectional view of the embodiment as shown in FIG. 1. FIG. 11 is a schematic perspective view showing a method of manufacturing the steam generating apparatus of the first embodiment.

Moreover, in this embodiment and other embodiments subsequent to this embodiment, a case where water is used as a liquid so as to generate steam will be described.

Reference symbol A in FIG. 1 depicts the steam generator which comprises a glass body 10 and a heater unit 20. In this glass body 10, a liquid tank portion 1 for storing the water and an evaporator portion 2 which is directly connected with the above-mentioned liquid tank portion 1 and heat the water supplied from the above-mentioned liquid tank portion 1 so as to generate the steam are formed. Further, in the above-mentioned glass body 10, a steam storage portion 3 is formed, which is directly connected with the above-mentioned evaporator portion 2 and stores the steam generated by the above-mentioned evaporator portion 2.

The transverse sectional area of the above-mentioned evaporator portion 2 is formed to be smaller than the transverse sectional area of the liquid tank portion 1. As described above, the above-mentioned evaporator portion 2 is formed so as to have the small transverse sectional area, so that it is possible to improve heating efficiency and to generate the steam at an early stage after heating.

As shown in FIG. 10, it is preferable that a side wall 2a of the evaporator portion 2 is made into a slope, and the transverse sectional area spreads or expands gradually from the liquid tank portion 1 side towards a steam storage portion 3 side, in other word, a shape of vertical section is formed into a trapezoid or a trapezium. As described above, the transverse sectional area of the evaporator portion 2 which is in contact with the liquid tank portion 1 is made to be smaller, so that a convection current of water in the liquid tank portion 1 and water of the evaporator portion 2 is controlled, to thereby generate the steam more easily and more efficiently.

A side end 3a of the above-mentioned steam storage portion 3 is formed in the shape of a circular arc, so that the steam stored in the steam storage portion 3 may not stagnate and the steam may be introduced into an outlet port 3b formed at the other end of the steam storage portion 3.

This steam storage portion 3 is provided for suppressing fluctuations in steam pressure, so as to suppress the fluctuations in steam pressure caused by fluctuations in the amount of water in the liquid tank portion 1 and fluctuations in the amount of the generated steam.

Moreover, within the above-mentioned glass body 10, a passageway 4 is formed, which outwardly leads the steam drawn through the outlet port 3b of the above-mentioned steam storage portion 3. This passageway 4 is divided into a circular are portion 4a and a diffusion portion 4b which spreads or expands gradually outwards.

A sucking tube B which is equivalent to the above-mentioned conventional sucking tube is preferably placed in a transitional position where the above-mentioned circular are portion 4a changes to the diffusion portion 4b, as indicated by dotted lines in FIG. 1, FIG. 2, and FIG. 8. By placing the above-mentioned sucking tube B in this position, the sucked liquid and the steam can be mixed and diffused more thoroughly. In addition, without providing the above-mentioned diffusion portion 4b, the passageway 4 may be formed to have the same sectional area, a nozzle may be provided at a terminal of the passageway, and a sucking tube may be placed in the vicinity thereof.

The above-mentioned glass body 10 is desirably a transparent glass body, a borosilicate glass body, or a soda glass body. More preferably, it is a transparent silica glass body.

As described above, it is constituted by the glass body 10, and therefore can be heated with the heater unit 20 by way of heat transfer and radiation, to thereby improve the thermal efficiency. Moreover, the glass has a low heat capacity, and therefore its temperature can rapidly be increased or decreased, thus preventing damages etc. due to a rapid change in temperature. Furthermore, it is excellent in corrosion resistance and may be manufactured inexpensively. In particular, the silica glass is preferable as compared with other glass, since it is excellent in corrosion resistance, high temperature deformation resistance, and chemical resistance when subjected to contact with the carbon wire heater body at a high temperature.

The above-mentioned liquid tank portion 1, the evaporator portion 2, the steam storage portion 3, and the passageway 4 are formed within the integral member. Further, without using a pipe (piping) etc., the liquid tank portion 1 and the evaporator portion 2 are connected directly, and the evaporator portion 2 and the steam storage portion 3 are connected directly. In other words, since the pipe (piping) is not used for connecting respective parts, it is possible to simplify the whole apparatus and reduce the heat capacity.

Now, with reference to FIG. 8, the above-mentioned sucking tube B and a connection part between the steam storage portion 3 and the passageway 4 will be described.

It is preferable that at the above-mentioned connection part, the above-mentioned passageway 4 is connected to the sucking tube B at an angle of 0 degree (both are parallel) to 45 degrees. For a connection angle formed in this way, when the steam moves from the circular are portion 4a to the diffusion portion 4b, a negative pressure takes place in the vicinity of an outlet of the sucking tube B, so that the liquid in the sucking tube is drawn whilst being sucked, and both are mixed.

In addition, the effect of sucking the above-mentioned liquid cannot be obtained, when the above-mentioned passageway 4 is formed at an angle which exceeds 45 degrees to the sucking tube B. Preferably, the above-mentioned passageway 4 is formed at an angle of not less than 5 degrees and not more than 20 degrees to the sucking tube B.

It is also preferable to form a diffusion plate 36 within the above-mentioned passageway 4, as shown in FIG. 9. A through hole 36a through which the steam passes is formed at the diffusion plate 36 which is fixed to a side wall of a passageway 4 by a support portion 36b. Preferably, this diffusion plate 36 is formed of glass and fixed to the side wall of the above-mentioned passageway 4 by welding.

Moreover, as shown in FIG. 1, this glass body 10 is provided with a pipe 5 which supplies water to the above-mentioned liquid tank portion 1 and a liquid pathway 10a which connects the pipe 5 and the liquid tank portion 1. The above-mentioned pipe 5 projects from a side surface of the glass body 10, and is connected to a water source (not shown). Further, the liquid pathway 10a is formed within the glass body 10.

Moreover, a thermocouple inserting hole 10b for inserting therein a thermocouple is formed above the outlet port 3b of the above-mentioned steam storage portion 3. Based on the temperature measured by this thermocouple, an applied voltage to the heater unit 20 (a carbon wire heater body 21) which will be described later is controlled so that the evaporator portion 2 etc. may reach and maintain a predetermined temperature.

As shown in FIG. 2, the above mentioned liquid tank portion 1, the evaporator portion 2, the steam storage portion 3, the outlet port 3b, the passageway 4, and the thermocouple insertion hole 10b are formed as recesses at the glass body 10.

By covering an opening side of the above-mentioned recesses by the heater unit 20 which will be described later, the liquid tank portion 1, the evaporator portion 2, the steam storage portion 3, the outlet port 3b, the passageway 4, and the thermocouple insertion hole 10b are formed as shown in FIG. 1.

Next, the heater unit 20 will be described.

The heater unit 20 is a heater in which the carbon wire heater body 21 is enclosed in the glass plate as shown in FIG. 1, FIG. 3, FIG. 4, and FIG. 5. In other words, a first glass plate 22 having formed therein a slot 22a where the carbon wire heater body 21 is accommodated is welded to a second glass plate 23 which covers the above-mentioned slot 22a, so that the carbon wire heater body 22a is enclosed in the glass plate.

Moreover, the above-mentioned carbon wire heater body 21 is arranged in a zigzag or meandering pattern, and wire portions thereof are flush with one another (arranged on the same plane). Al a sealing terminal portion 24, the above-mentioned carbon wire heater body 21 is connected with an outer connection line 25 through which electric power is supplied.

The above-mentioned first glass plate 22 and the second glass plate 23 are desirably transparent glass bodies, borosilicate glass bodies, and soda glass bodies. More preferably, they are transparent silica glass bodies.

Since they are constituted by the glass plates in this way, they allow heating by way of heat transfer and radiation, to thereby improve the thermal efficiency. Moreover, the glass has a low heat capacity, and therefore its temperature can rapidly be increased, thus preventing damages etc. due to a rapid change in temperature. Furthermore, they are excellent in corrosion resistance, and may be manufactured inexpensively.

In particular, the silica glass body is preferable as compared with other glass, since it is excellent in corrosion resistance, high temperature deformation resistance, chemical resistance, etc. when subjected to contact with the carbon wire heater body at a high temperature.

As shown in FIG. 1, the heater unit 20 is constructed to be welded to the side surface of the glass body 10, to close the recesses which form the above-mentioned liquid tank portion 1, the evaporator portion 2, the steam storage portion 3, the outlet port 3b, the passageway 4, and the thermocouple insertion hole 10b, and to heat the liquid tank portion 1, the evaporator portion 2, the steam storage portion 3, and the passageway 4.

The above-mentioned carbon wire heater body 21 is constructed to heat the liquid tank portion 1, the evaporator portion 2, the steam storage portion 3, and the passageway 4, but different parts need different temperatures. Therefore, the above-mentioned carbon wire heater body 21 is formed densely for a part which needs a high temperature, while the above-mentioned carbon wire heater body 21 is formed in sparsely for a part in which a low temperature is sufficient.

For example, the carbon wire heater body 21 is provided to have a formation pattern such that the steam storage portion 3 may be heated to 130–150, when a temperature at the evaporator portion 2 is 100.

Referring now to FIG. 5, the carbon wire heater body 21 will be described. As shown in FIG. 5, the above-mentioned carbon wire heater body 21 comprises braided cords or plaited cords formed by weaving or knitting a plurality of fiber bundles in which carbon fibers are bundled.

It is preferable that the carbon wire heater body 21 is woven or knitted into a braided cord with a diameter of 1.0–2.5 mm or a shape of a plaited cord by using about 10 fiber bundles, each of which bundles approximately 800 to 3500 carbon single fibers having a diameter of between about 5 and 15 m, for example, carbon single fibers with a diameter of 7.m.

Preferably, a weaving width of the carbon wire heater body 21 is about 2–5 mm, and a length of the fuzz 21a of the carbon single fibers on a surface of the carbon wire heater body 21 is approximately 0.5–2.5 mm.

In this way, the fuzz 21a of the carbon single fibers is formed so that a glass member is substantially brought into contact with the fuzz 21a, whereby a touch area in contact with a body part of the carbon wire heater body 21 can be reduced, a reaction between silica ($SiO_2$) and carbon (C) can be minimized, and durability can be improved.

Moreover, from viewpoints of heating homogeneity, durability, stability, etc., and from a viewpoint of avoiding dust generating, the carbon single fibers which constitute the carbon wire heater body 21 are preferably of high purity. It is preferable that an amount of impurities contained in the carbon single fibers as ash content (JIS R 7223-1979) is not greater than 10 ppm, more preferably not greater than 3 ppm.

In addition, it is preferable that specific resistance of the carbon wire heater body 21 is 10 to 20.m at a temperature of 1000. Since the specific resistance is from 10 to 20.m, a current can be from 5A to 15A, and a voltage can be about 100V. For this reason, the current may be reduced and not apply a burden to a sealing terminal portion in which the pinch seal is carried out. Furthermore, an electric power unit can be made compact by setting the voltage to 100V or less.

The reason why such a carbon wire heater body 21 is used is that, since the heat capacity is low as compared with a conventional metal heater, for example, it is possible to raise and reduce the temperature rapidly. In particular, a steam generator A comprises the glass body, so that it is possible to raise and reduce the temperature rapidly. Unlike the metal heater, resistance of the carbon wire heater body 21 has a tendency to become high at an ordinary temperature and become low at a high temperature. As a result, even when the temperature is raised rapidly, an overcurrent does not flow so that accidents, such as a blown fuse etc. can be prevented.

Furthermore, since the carbon wire heater body 21 is formed by plaiting carbon single fibers, it is not easily cut; its resistance may not substantially change, even if several fibers are cut. Thus, the carbon wire heater body 21 is suitable as a heater for the steam generating apparatus.

Next, a sealing terminal portion 24 will be described with reference to FIGS. 1, 3, 6, and 7. In addition, FIG. 6 shows a lip portion (glass plate 22 side) of the sealing terminal portion 24, and FIG. 7 shows a back end part of the sealing terminal portion 24.

As shown in FIGS. 6 and 7, a glass tube 26 is provided which accommodates therein an end of the carbon wire heater body 21; a wire carbon member 27 is provided which is compressed and accommodated in the above-mentioned glass tube 26, and which sandwiches or holds the end of the above-mentioned carbon wire heater body 21. This glass tube 26 is accommodated inside the glass tube 29.

In addition, the wire carbon member 27 which sandwiches or holds the end of the carbon wire heater body 21 is formed of a material similar to or homogeneous with the carbon wire heater body 21. A plurality of, such as 2 to 4, the above mentioned carbon wire heater bodies 21 are bundled. Further, three bundles of the carbon wire heater bodies 21 form the wire carbon member 27. The above-mentioned carbon wire heater body 21 is arranged to be located among these three uniform wire carbon bundles and substantially in the center of the above-mentioned glass tube 26.

The back end of the sealing terminal portion 24 comprises an inner connection line 28 whose end is accommodated in the above-mentioned glass tube 26 and which is made of Mo (molybdenum), for supplying electric power, and sandwiched or held by the wire carbon member 27; a Mo (molybdenum) foil 30 electrically connected with the above-mentioned inner connection line 28; and an outer connection line 25 which is made of Mo (molybdenum) and electrically connected to the Mo (molybdenum) foil 30. The Mo (molybdenum) foil 30 is subjected to so-called pinch seal at the above-mentioned glass tube 29.

A tip portion of the above-mentioned glass tube 29 is welded to the glass plate 22 and a back end part of the above-mentioned glass tube 29 is subjected to the pinch seal, so that the above-mentioned glass tube 29 is hermetically sealed. In addition, the inside of the glass tube 29 is filled with nitrogen gas so as to inhibit the carbon wire heater body 21 etc. from being oxidized.

As shown in FIG. 3, a reflection coating or a reflection member 19 is provided on the glass plate 22 in which the carbon wire heater body 21 of the heater unit 20 is enclosed.

In other words, the reflection coating or the reflection member 19 is provided on the side surface of the glass plate 22 which is opposite to an arrangement side of the glass body 10. The reflection coating or the reflection member 19 may be formed on the entire side surface of the glass plate 22 or may be formed only at a position corresponding to a position where the evaporator portion 2 and the steam storage portion 3 etc. are formed.

The reflection coating or the reflection member 19 is thus provided, so that the evaporator portion 2 etc. can be efficiently heated. For example, the reflection coating can be an Al film, an Au film, a TiN film, a Si film, an $Al/Al_2O_3$ multilayer film, an $Al/SiO_2$ multilayer film, a Cr/TiN multilayer film, a $Cr/TiN/TiO_2$ multilayer film, or a $Si/SiO_2$ multilayer film. Moreover, the reflection member can be an Al foil or an Au foil.

The above-mentioned reflection coating 19 can be formed on a surface of the glass plate 22 by means of a vapor deposition process or a CVD (Chemical Vapor Deposition) process, and the reflection member 19 can be formed by means of adhering or pasting. Desirably, a film thickness of the above-mentioned reflection coating 19 is not less than 10.m and not more than 500.m. This is because there is a possibility that good reflection could not be provided when the thickness is not more than 10.m, or the coating may be peeled off when the thickness is not less than 500.m.

In addition, it is preferable that surface roughness of the glass plate 22 on which the reflection coating 19 is formed is from 0.1.m to 500.m in Ra (Arithmetic Average Roughness). The reflection coating tends to be peeled off when its surface roughness is not more than 0.1.m in Ra, and heat conduction is reduced when it is not less than 500.m in Ra, this is not preferred.

It is preferable that the above-mentioned reflection coating or the reflection member 19 is provided within a recess which is formed at a side surface of the glass plate 22 and covered with glass. Since the reflection coating or the reflection member 19 is formed inside the recess, it is possible to prevent it from being peeled off or dropping.

Next, operation of the steam generator A will be described.

A predetermined quantity of water is supplied through the pipe 5 and the liquid pathway 10a to the liquid tank portion 1. In this state, when the electric power is supplied to the carbon wire heater body 21, the evaporator portion 2 is heated and steam is generated. Especially, since the transverse sectional area of the evaporator portion 2 is smaller than that of the liquid tank portion 1, the steam can be generated efficiently in the evaporator portion 2.

The thus generated steam is stored in the steam storage portion 3 temporarily and supplied through the outlet port 3b to the passageway 4. At this stage, since the steam storage portion 3, the outlet port 3b, and the passageway 4 are heated by the above-mentioned carbon wire heater body 21, steam condensation can be inhibited. In addition, when the sucking tube B is placed in the transition position where the above-mentioned circular are portion changes to the diffusion portion, the liquid and steam which are sucked through the sucking tube B may be mixed and diffused thoroughly.

Next, the method of manufacturing the steam generator A will be described with reference to FIG. 1, FIG. 2. FIG. 3, FIG. 6, FIG. 7, and FIG. 11.

Firstly, the recess including the liquid tank portion 1, the evaporator portion 2, the steam storage portion 3, the outlet port 3b, and the passageway 4 is formed in the glass body 10. The liquid pathway 10a connected to the liquid tank portion 1 and the pipe 5 connected to this liquid pathway 10a are also formed in the above-mentioned glass body 10. Further, the thermocouple insertion hole 10b for inserting therein the thermocouple is formed.

On the other hand, the slot 22a for containing therein the carbon wire heater body 21 is formed in the glass plate 22. The above-mentioned carbon wire heater body 21 is disposed in the above-mentioned slot 22a.

Then, a mirror finishing process is carried out for a slot formation side (a surface where the carbon wire heater body 21 is provided) of the above-mentioned glass plate 22, and for a surface of the glass plate 23 (the surface being opposite lo or facing the surface of the slot formation side of the glass plate 22). Another mirror finishing process is carried out for a surface on the recess formation side of the glass body 10 and for a surface of the glass plate 23 (the surface being opposite to or facing the surface on the recess formation side of the glass body 10).

Then, as shown in FIG. 11, the three members are stacked and are placed in a high temperature processing furnace so that adhesion surfaces may be horizontal. The three members are welded and unified by applying a load of 0.1 kgf/cm$^2$ to them at 1450.

After the fusion welding, the end of the carbon wire heater body 21 is arranged to be located among three uniform wire carbon bundles (the wire carbon member 27) and substantially in the center of the above-mentioned glass tube 26 as shown in FIG. 6. Then, the above-mentioned glass tube 26 is accommodated in the glass tube 29 and the above-mentioned glass tube 29 is welded and fixed to the back of the glass plate 21.

As shown in FIG. 6 and FIG. 7, an end of the inner connection line 28 is inserted into the wire carbon bundles (the wire carbon member 27), and the other end is fixed to an end of the Mo foil 30. The outer connection lines 25 are fixed to the other end of the Mo foil 30. Under a nitrogen atmosphere, the end of the glass tube 29 is subjected to the pinch seal and hermetically sealed at a pressure of 100 torr inside the glass tube 29.

Finally, the thermocouple is inserted into the thermocouple insertion hole 10b so as to complete the steam generator.

As described above, as for the steam generator A in accordance with the above embodiment, the above-mentioned liquid tank portion 1, the evaporator portion 2, the steam storage portion 3, the passageway 3, and liquid pathway 10a are formed within the integral member of the translucent material. Without using a pipe etc., the liquid tank portion 1 and the evaporator portion 2 are connected directly, and the evaporator portion 2 and the steam storage portion 3 are connected directly. Thus, since a pipe is not used for connecting respective portions, the whole apparatus can be simplified, its heat capacity can be made small, and the rapid heating can be performed. As a result, it is possible to shorten the time period between the start of heating and the start of atomizing after the steam is generated.

In particular, since the steam generator A is constituted by glass, it allows heating by way of heat transfer and radiant heat by means of the heater unit 20, thus improving the thermal efficiency. Moreover, the glass has a low heat capacity, and therefore its temperature can rapidly be increased or decreased, thus preventing damages etc. due to the rapid change in temperature. Furthermore, it has an excellent resistance to corrosion and may be manufactured inexpensively.

Figure 12A:
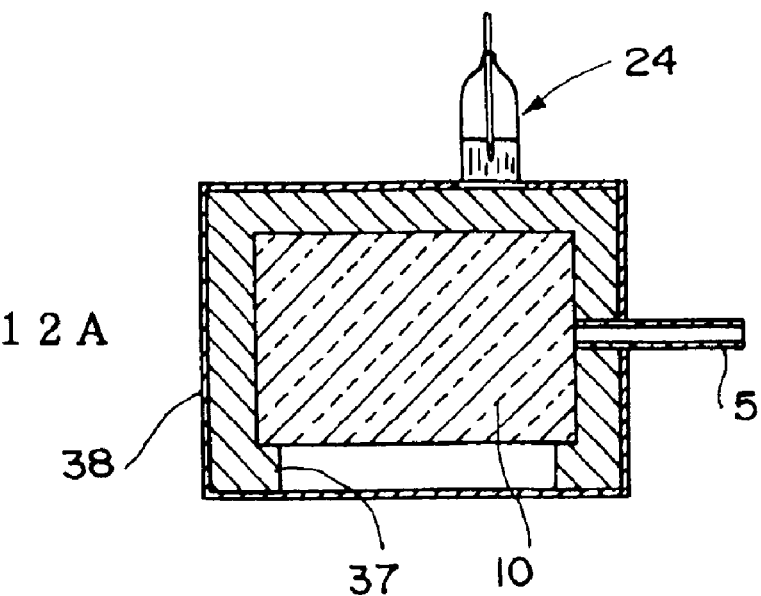
FIG. 12A is a cross-sectional view along the line I—I in FIG. 12A.
Figure 12B:
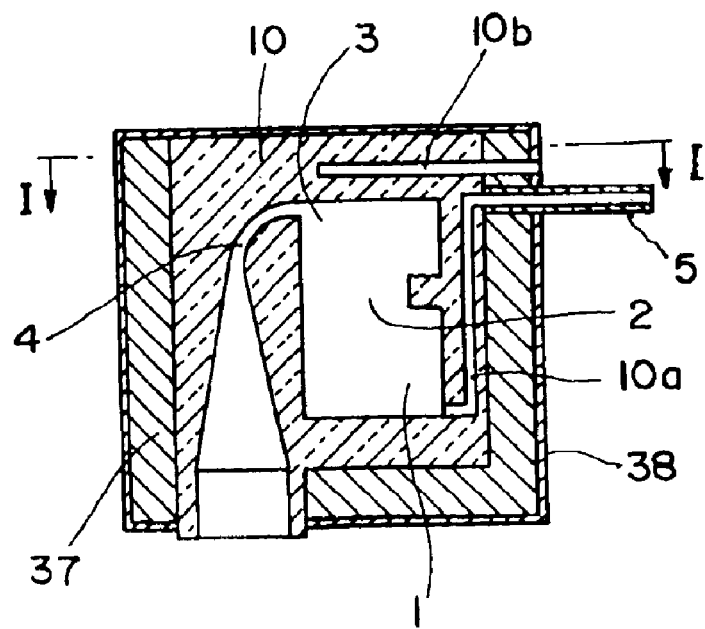
FIG. 12B is a vertical sectional view.

Next, a second embodiment of the steam generator in accordance with the present invention will be described with reference to FIG. 12. In addition. FIG. 12 show a state where the steam generator is accommodated, together with the thermal insulation material, within the metal casing, FIG. 12A is a cross-sectional view along the line I—I in FIG. 12B, and FIG. 12B is a vertical sectional view.

This embodiment is such that the steam generator of the above-mentioned first embodiment is surrounded by a thermal insulation material 37.

In other words, the glass body 10 and the heater unit 20 are surrounded by the thermal insulation material 37, such as glass wool, a fiber flux board, a porous-ceramics block, or rock wool, and further contained in a metal casing 38.

The glass body 10 and the heater unit 20 are thus surrounded by the thermal insulation material 37, so that it is possible to perform the heating efficiently. Since the steam generator is accommodated in the metal casing 38, it is possible to protect the steam generator against an impact etc. In addition, when the thermal insulation material 37 is glass wool etc., it functions as a so-called shock absorbing material, thus protecting the steam generator against the impact etc.

Figure 13:
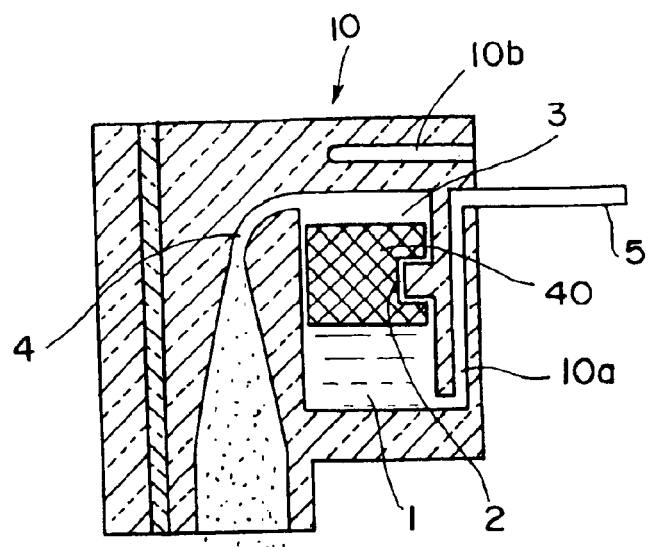
FIG. 13 is a schematic vertical sectional view showing a third embodiment of the steam generator in accordance with the present invention.
Figure 14:
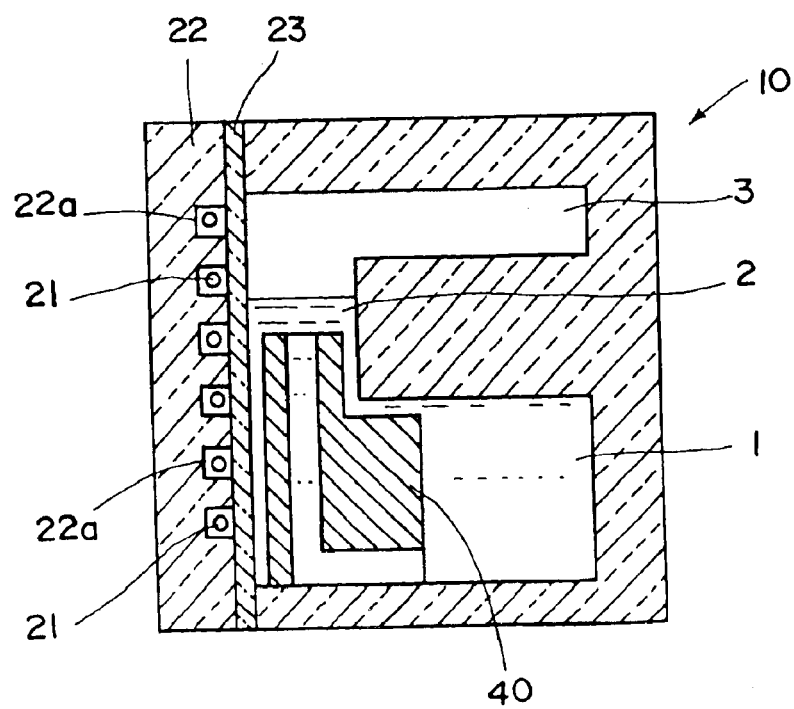
FIG. 14 is a schematic vertical sectional view showing a modification of the third embodiment as shown in FIG. 13.

Next, a third embodiment of the steam generator in accordance with the present invention will be described with reference to FIGS. 13 and 14. In addition, FIG. 13 is a schematic vertical sectional view showing a third embodiment of the steam generator in accordance with the present invention. FIG. 14 is a schematic vertical sectional view showing a modification of the third embodiment as shown in FIG. 13.

This embodiment is characterized by being provided with a porous body 40 at the above-mentioned evaporator portion 2 and in the liquid tank portion 1.

In other words, as shown in FIG. 13, when the porous body 40 is provided at the above-mentioned evaporator portion 2 and in the liquid tank portion 1, water supply to the evaporator portion 2 is stabilized by capillary phenomena in the porous body 40. Moreover, bumping in the evaporator portion 2 and the liquid tank portion 1 can be prevented. In addition, although a lower end part of the porous body 40 is located in an upper part of the liquid tank portion 1 in FIG. 13, the lower end part of the porous body 40 may be located at a lower part (bottom) of the liquid tank portion 1.

Moreover, as for the porous body 40, porous glass, porous SiC, a carbon porous body, carbon felt, a porous brick, and glass wool yarn can be used. However, when the porous SiC, the carbon porous body, etc. are used as the porous body 40, it is preferable that the whole porous body 40 is provided in the water, in order to prevent the porous body 40 from being oxidized in contact with the steam.

As shown in FIG. 14, when the porous body 40 is formed of a material having a heat capacity to some extent (endothermic body) such as an SiC material, a carbon material, etc. and the porous body 40 is provided at the above-mentioned evaporator portion 2 and in the liquid tank portion 1, it is possible to store the heat from the heater unit 20 and improve the heat transfer efficiency with respect to water.

The porous body 40 in this case may only have a certain heat capacity, and its material is not particularly limited in this regard. However, the porous body 40 is preferably provided in the water, in order to prevent the porous body 40 from being oxidized in contact with the steam when a carbon fiber etc. is used as the porous body 40. Moreover, the pores in the porous body 40 increase the touch area in contact with water, to thereby improve a steam generating efficiency.

Figure 15:
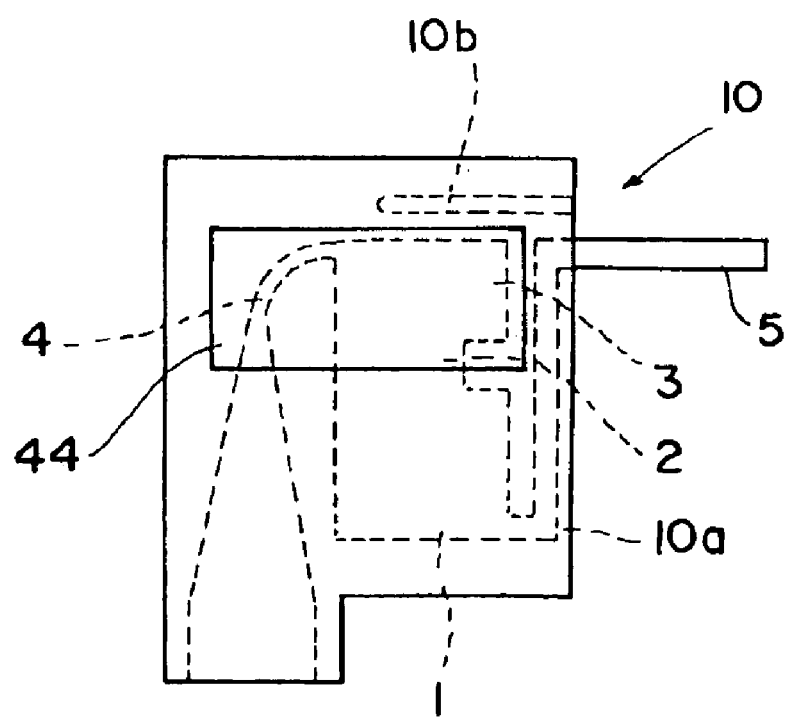
FIG. 15 is a schematic side view showing a fourth embodiment of the steam generator in accordance with the present invention.

Next, a fourth embodiment of the steam generator in accordance with the present invention will be described with reference to FIG. 15. In addition, FIG. 15 is a schematic side view showing the fourth embodiment.

This embodiment is characterized in that a heat equalizing plate 44 or a heat equalizing coating 44 is formed, between the above-mentioned heater unit 20 and the above-mentioned glass body 10, which equalizes heat conduction from the above-mentioned heater unit to each part which is heated by the above-mentioned glass body.

In this way, the heat equalizing plate 44 or the heat equalizing coating 44 is provided between the above-mentioned heater unit 20 and the above-mentioned glass body 10, in particular, in the side positions of the evaporator portion 2 and the steam storage portion 3 of glass body 10, so that the temperature at each of the above-mentioned parts may be equalized and the thermal efficiency may be improved.

A glass-like carbon board and a carbon board can be used as the above-mentioned heat equalizing plate 44. Moreover, carbon, carbon powder, and a SiC film can be used as the heat equalizing coating 44. In addition, as described above, the film thickness is desirably not less than 10.m and not more than 500.m. This is because there is a possibility that good heat equalization could not be provided when the thickness is not more than 10.m, or the coating may be peeled off when it is not less than 500.m. The heat equalizing member can be formed by means of adhering or pasting.

It is preferable that the above-mentioned heat equalizing plate 44 or the heat equalizing coating 44 is provided within a recess which is formed at a side surface of the glass plate 22 and covered with glass. Since the heat equalizing plate or the heat equalizing coating is formed within the recess, it is possible to prevent it from being peeled off or dropping.

Figure 16:
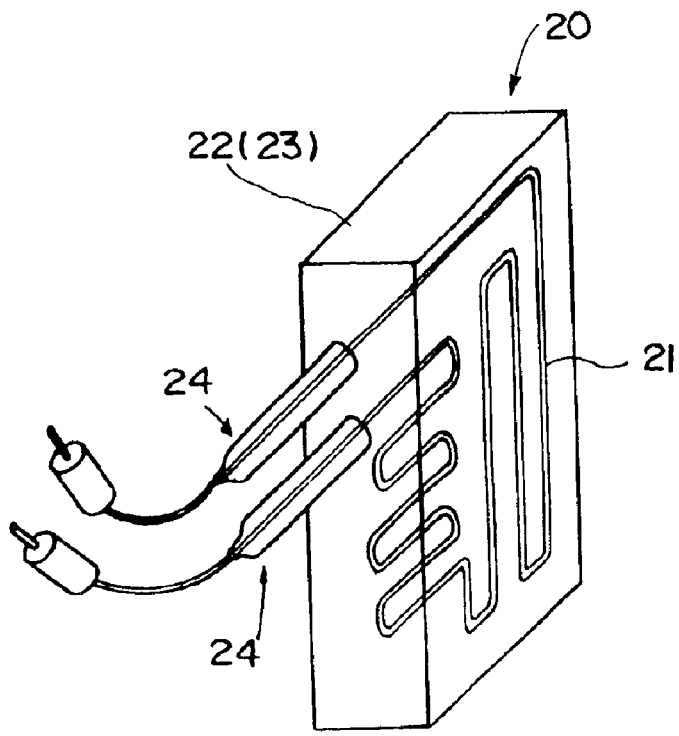
FIG. 16 is a schematic side view showing a fifth embodiment of the steam generator in accordance with the present invention.

Next, a fifth embodiment of the steam generator in accordance with the present invention will be described with reference to FIG. 16. In addition, FIG. 16 is a perspective view showing the fifth embodiment.

This embodiment is characterized in that the sealing terminal portion 24 is formed at a side surface perpendicular to the slot formation side (where the carbon wire heater body 21 is provided) of the glass plate 22. Since the sealing terminal portion 24 is thus formed at the side surface perpendicular to the slot formation side (where the carbon wire heater body 21 is provided) of the glass plate 22, the reflection coating or the reflection member as in the first embodiment or a ninth embodiment (which will be described later) can be provided on the entire side surface, and the thermal efficiency can be improved.

Next, a sixth embodiment of the steam generator in accordance with the present invention will be described with reference to FIG. 17. In addition, FIGS. 17 are cross-sectional views showing the sixth embodiment, FIG. 17A is a cross-sectional view of the main part of the heater unit 20, and FIG. 17B is another cross-sectional view of the main part of the heater unit 20 showing a state where two carbon wire heater bodies 21 are provided.

Figure 17A:
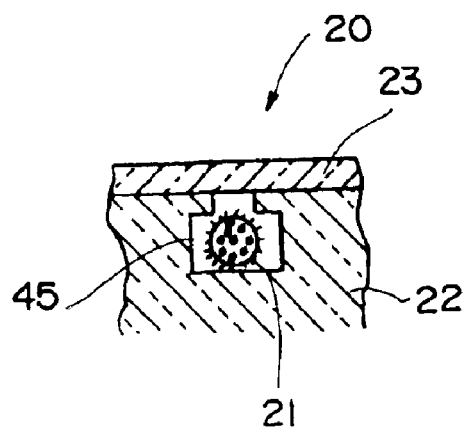
FIG. 17A is a cross-sectional view of the main part of the heater unit.

In this embodiment the slot 45 which contains therein the carbon wire heater bodies 21 has a modified reverse T-shape as shown in FIG. 17A. Since the slot 45 is thus formed in the shape of reverse T character, once the carbon wire heater body 21 is accommodated in the slot 45, the carbon wire heater body 21 cannot protrude out of the above-mentioned slot 45, and the carbon wire heater body 21 can be easily laid.

Figure 17B:
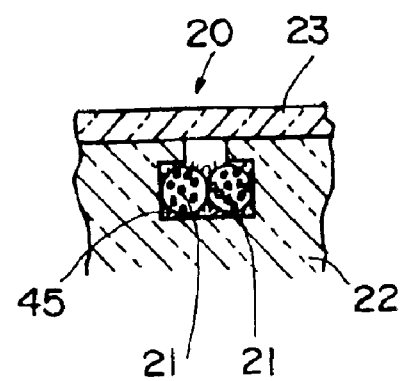
FIG. 17B is a cross-sectional view of the main part of the heater unit showing a case where two carbon wire heater bodies are arranged.

Moreover, two carbon wires heater bodies 21 may be contained in the above-mentioned slot 45 as shown in FIG. 17B. As described above, when two carbon wires heater bodies 21 are disposed, even if an accident, such as an open circuit, occurs at one carbon wire heater body, it is possible to maintain the heating function.

Next, a seventh embodiment of the steam generator in accordance with the present invention will be described with reference to FIG. 18.

Figure 18A:
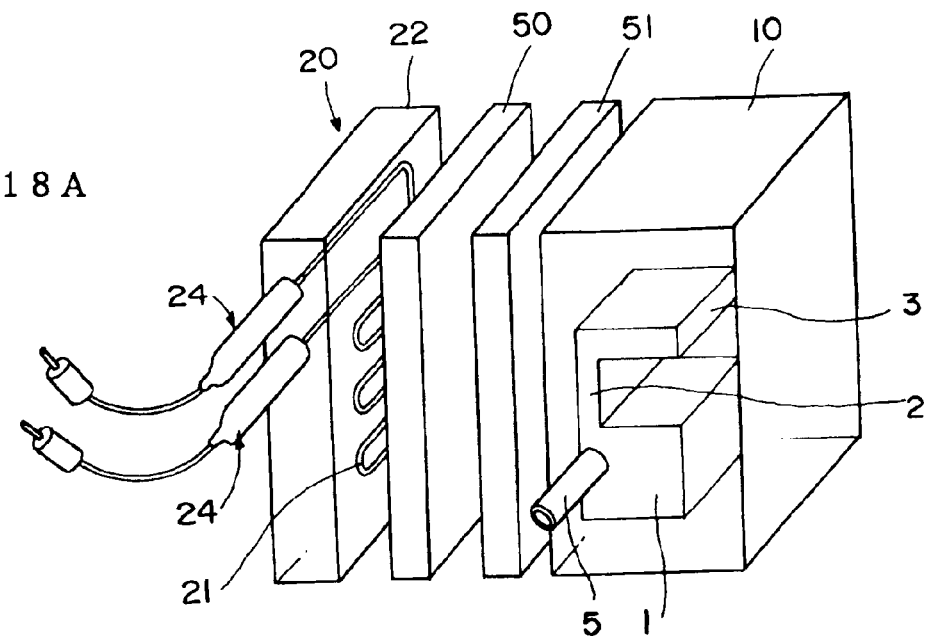
FIG. 18A is a schematic perspective view.

This embodiment is characterized in that the glass body 10 and the heater unit 20 are not integrated by welding but formed to be separable. In other words, as shown in FIG. 18A, the above-mentioned carbon wire heater body 21 is placed in the slot 22a of the glass plate 22, to which a glass plate 50 is welded so as to form the heater unit 20.

On the other hand, the liquid tank portion 1, the evaporator portion 2, the steam storage portion 3, the outlet port 3b, the passageway 4, and the thermocouple insertion hole 10b are formed in the glass body 10 as the recess. The glass plate 51 is welded to the recess side surface of this glass body 10.

Figure 18B:
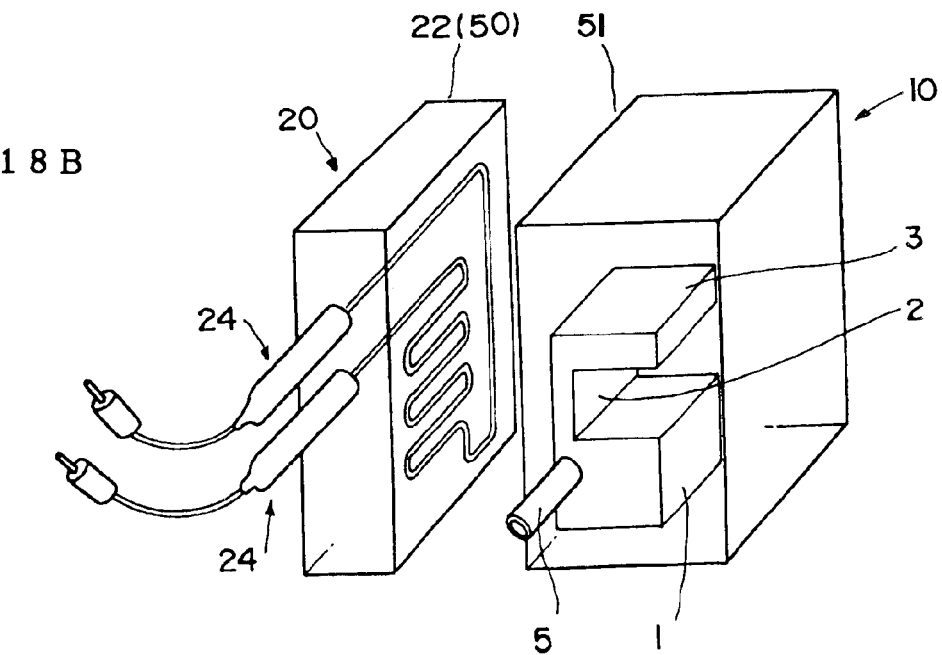
FIG. 18B is another schematic perspective view.

While the above-mentioned heater unit 20 and glass body 10 are separately formed, as shown in FIG. 18B.

The heater unit 20 and the glass body 10 are surrounded by the thermal insulation material 37 as shown in the second embodiment of FIG. 12, further the glass body 10 and the heater unit 20 are accommodated in the metal casing 38.

As described above, since the heater unit 20 and the glass body 10 are formed separately, when breakage etc. occur, the breakage may be easily repaired by only replacing them. Moreover, if the tank unit 1 and the evaporator portion 2 are fouled due to adhesion of a dissolved material thereto, for example, the glass body 10 can be cleaned easily.

Figure 19:
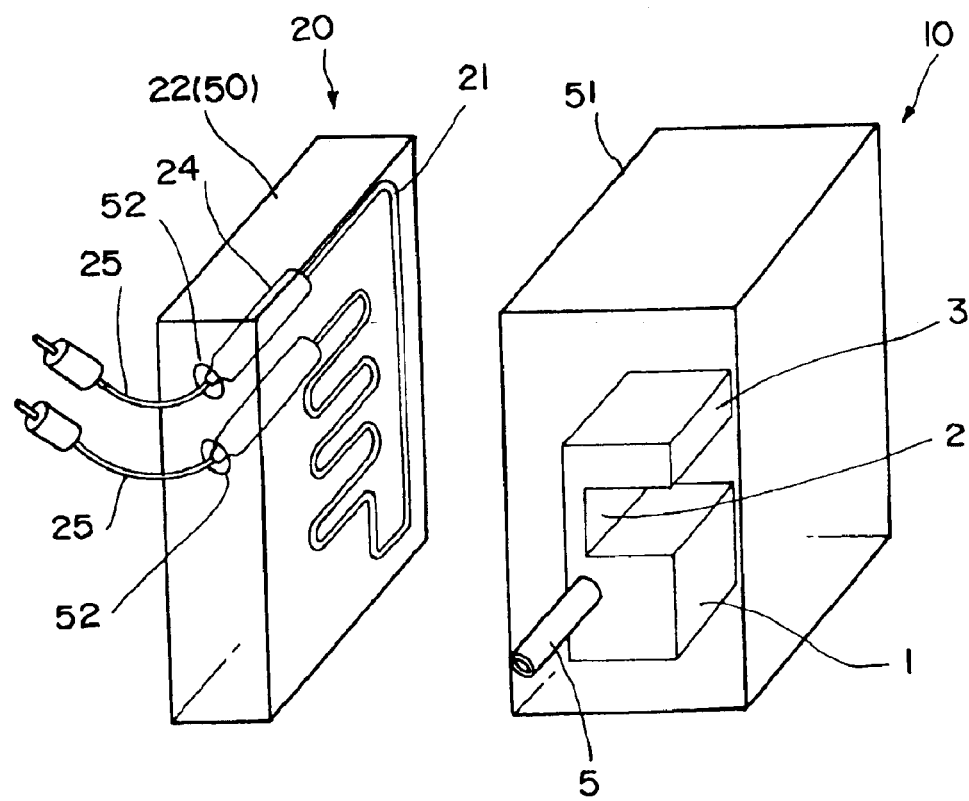
FIG. 19 is a schematic perspective view showing an eighth embodiment of the steam generator in accordance with the present invention.

Next, an eighth embodiment of the steam generator in accordance with the present invention will be described with reference to FIG. 19. This embodiment is characterized in that the sealing terminal portion 24 is accommodated in the glass plate 22 (50), without the sealing terminal portion 24 projecting from the heater unit 20, unlike the first embodiment.

Since the sealing terminal portion 24 is thus contained in the glass plate 22 (50), the protection of the sealing terminal portion 24 can be attained, and it is possible to prevent the breakage etc. In addition, the outer connection lines 25 extended from the sealing terminal portion 24 is constructed to be pulled out of an opening 52.

Next, a ninth embodiment of the steam generator in accordance with the present invention will be described with reference to FIG. 20. In addition, FIG. 20 is, a view showing the ninth embodiment, FIG. 20A is a schematic perspective view showing the heater unit, and FIG. 20B is a schematic perspective view showing a modification.

In this embodiment, heat emitted to a back surface of the carbon wire heater body 21 is collected so that the glass body 10 is heated. Therefore, the thermal efficiency can be improved as compared with that in the first embodiment.

Figure 20A:
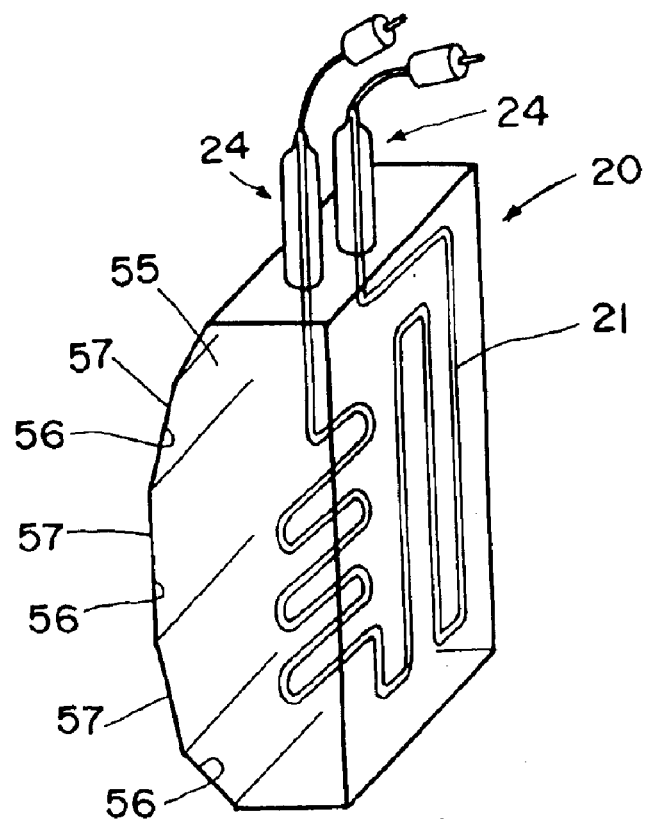
FIG. 20A is a schematic perspective view showing the heater unit.
Figure 20B:
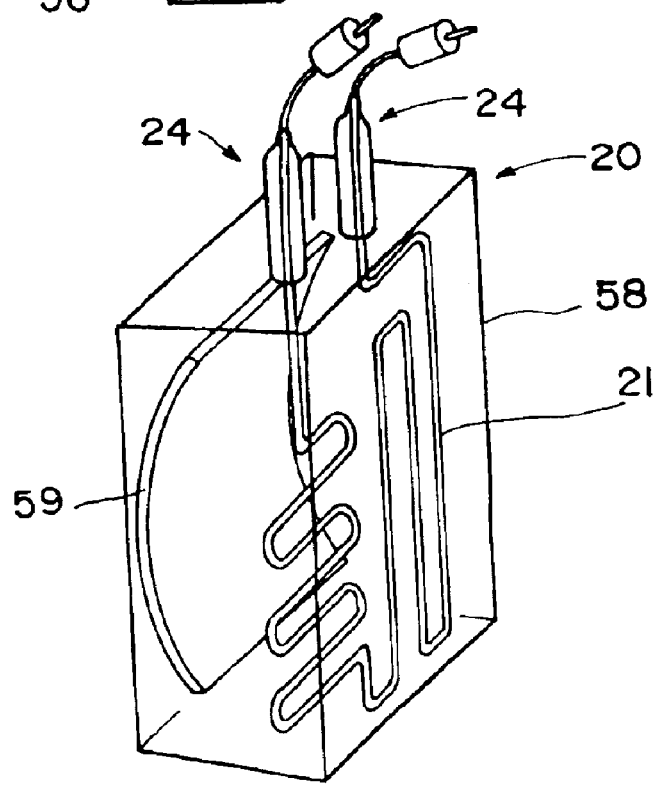
FIG. 20B is a schematic perspective view showing a modification.

In other words, as shown in FIG. 20A, a back surface of the glass plate 55 in which the above-mentioned carbon wire heater body 21 is enclosed is formed to have a plurality of surfaces 56 which each have a predetermined angle. The back surface of the glass plate 55 is a side surface which opposes the side to be welded to the glass body 10. The reflection coating 57 or the reflection member 57 is provided at the plurality of surfaces 56.

Since the back surface of the glass plate 55 in which the carbon wire heater body 21 is enclosed is formed in this way so as to have the plurality of surfaces 56 which each have the predetermined angle, and since the reflection coating 57 or the reflection member 57 is formed at the surfaces 56, the heat can be collected towards the glass body 10, in particular any one of or some of the evaporator portions 2, the steam storage portions 3, and the passageway 4 can arbitrarily be heated effectively and simultaneously.

Moreover, as shown in FIG. 20B, in the heater unit 20 in which the carbon wire heater body 21 is enclosed, if the reflection film or the reflection member 59 is embedded in a glass plate 58 such that the carbon wire heater body 21 which forms the heater unit 20 is between the reflection film or the reflection 59 and the surface to be welded to the glass body 10, the effects similar to the above can be obtained.

The reflection film or the reflection members 57 and 59 may be formed on the entire side surface of the glass body 10, or may be formed only in a position corresponding to a formation position of the evaporator portion 2 and the steam storage portion 3, etc.

The evaporator portion, the steam storage portion, etc. can be efficiently heated by providing the reflection coating or the reflection members 57 and 59 in this way. The reflection film or coating may be, for example, the Al film, the Au film, the TiN film, the Si film, the $Al/Al_2O_3$ multilayer film, the $Al/SiO_2$ multilayer film, the Cr/TiN multilayer film, the $Cr/TiN/TiO_2$ multilayer film, or the $Si/SiO_2$ multilayer film. Further, the Al foil and the Au foil can be used as the reflection member.

The above-mentioned reflection coating 57 may be formed on at least one surface of the heater unit 20 by means of the vapor deposition process or the CVD process. Moreover, the film thickness of the above-mentioned reflection coating 57 is desirably not less than 10.m and not more than 500.m. This is because there is a possibility that good reflection could not be provided when the thickness is not more than 10.m, or the coating may be peeled off when it is not less than 500.m.

In addition, the surface roughness of the glass body which forms the reflection coating 57 is preferably 0.1.m to 500.m in Ra. The reflection coating tends to be peeled off when its surface roughness is not more than 0.1.m in Ra, and heat conduction is reduced when it is not less than 500.m in Ra, this is not preferred.

Although the above embodiment is described with reference to the case where the steam is generated, the present invention is not limited thereto, and may naturally use another liquid instead of water. Moreover, the above embodiments have been described as forming the above-mentioned liquid tank portion, the evaporator portion, the steam storage portion, the passageway, and the liquid pathway in the glass body. However, according to the present invention they may only be formed in an integral member made of a translucent material, other than the glass body.

Moreover, although the components of the "glass" for the glass body, the glass plate, the glass tube, etc. are not specified in the above embodiments, the most preferable "glass" is silica glass as described above:

Although the "silica glass" is not specified in the embodiments, the above-mentioned glass body, the glass plate, the glass tube, etc. may naturally include those made of silica glass.

Although the above embodiments have been described by way of the case where the thermocouple is disposed above the outlet port 3b of the steam storage portion, the thermocouple may be provided in the vicinity of the evaporator portion.

According to the present invention, the steam can be supplied efficiently and stably, and moreover the steam can be generated in a short period of time, the structure is simplified, and a steam generator which simplifies its maintenance can be provided.

Figure 21:
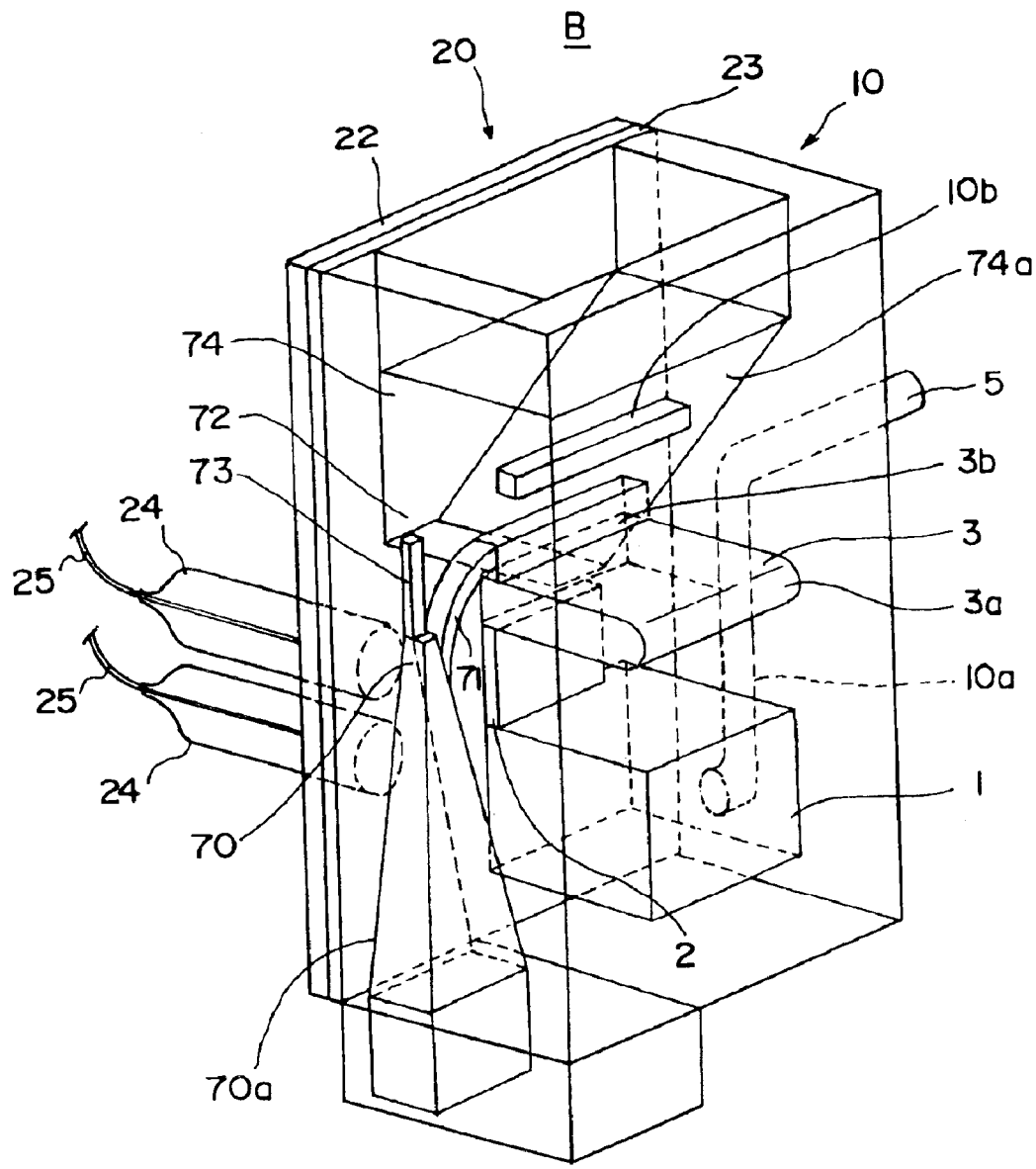
FIG. 21 is a perspective view showing a first embodiment of a mixer in accordance with the present invention.
Figure 22:
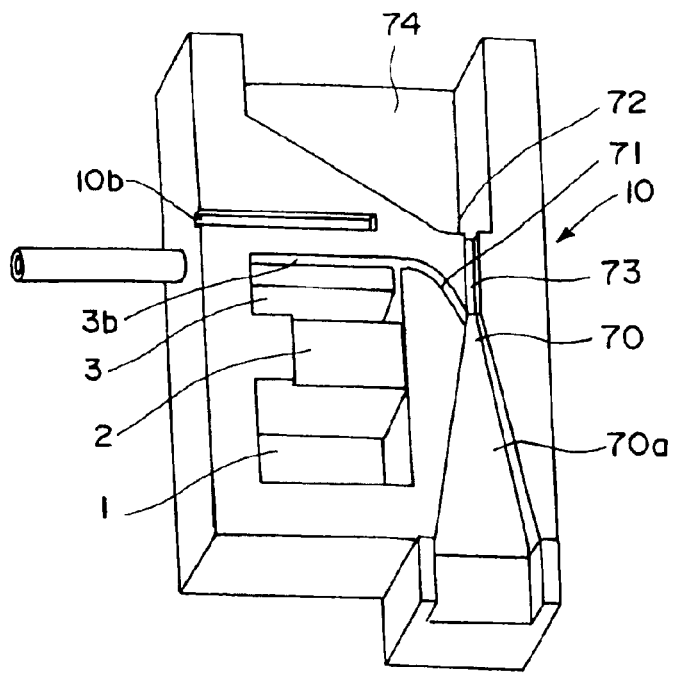
FIG. 22 is a perspective view of a silica glass body as shown in FIG. 21.
Figure 23A:
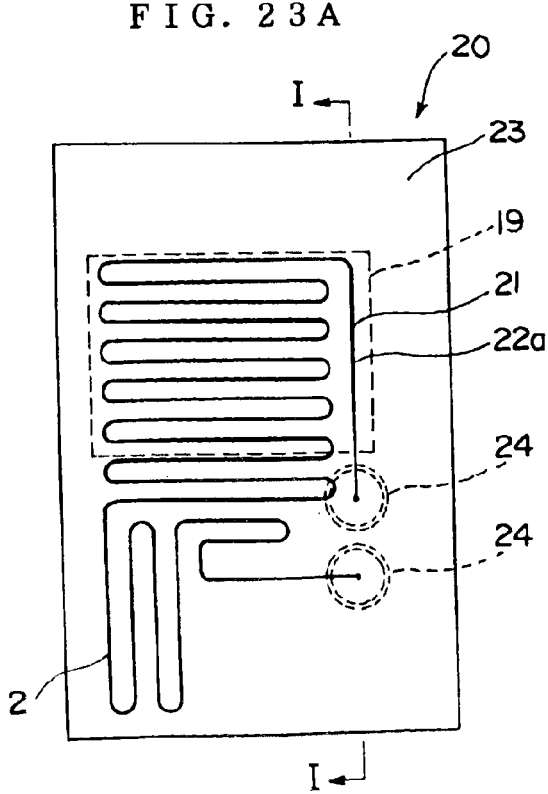
FIG. 23A is a view from the heater forming side.
Figure 23B:
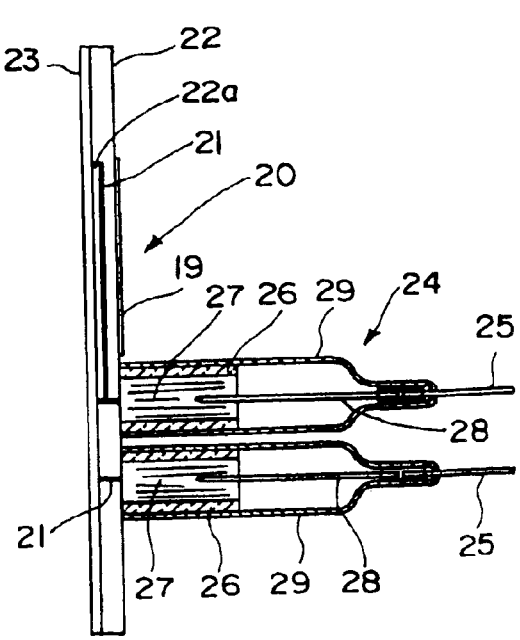
FIG. 23B is a cross-sectional view along the line I—I in FIG. 23A.
Figure 24:
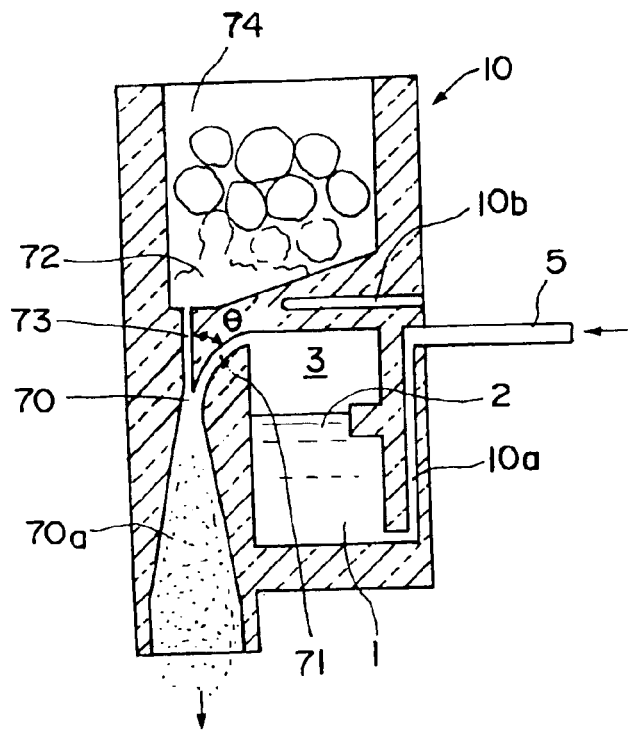
FIG. 24 is a schematic vertical sectional view of the embodiment as shown in FIG. 21.
Figure 25:
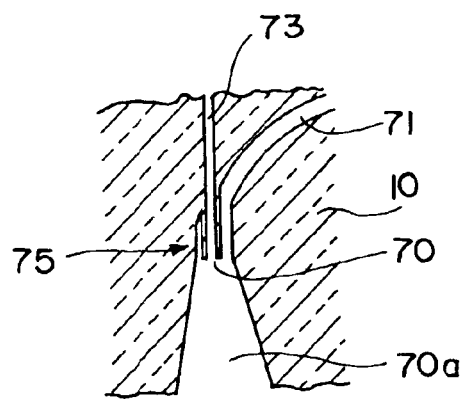
FIG. 25 is a cross-sectional view showing a modification of a mixing portion.
Figure 26A:
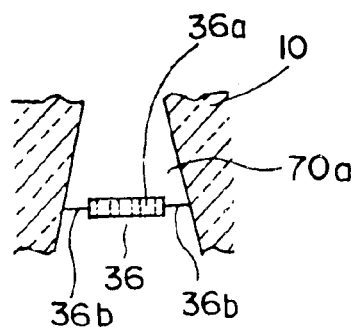
FIGS. 26A and 26B show the diffusion plate and are respectively a front view and a side view.
Figure 26B:
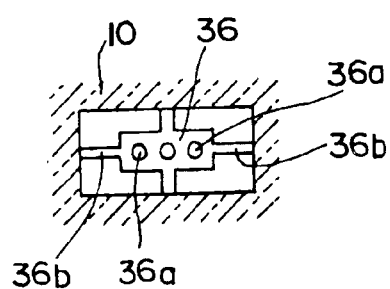
Figure 27:
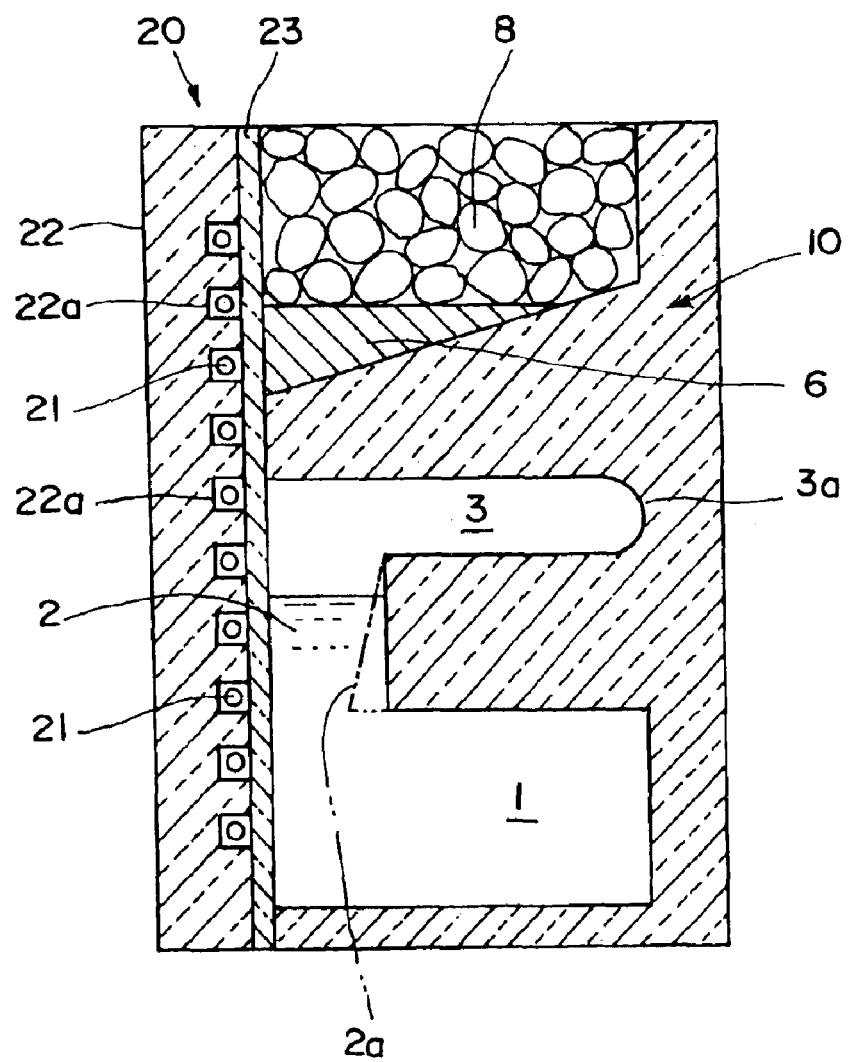
FIG. 27 is a schematic vertical sectional view showing a modification of an evaporator portion in the first embodiment of the mixer as shown in FIG. 21.

Next, a first embodiment of the mixer, in accordance with the present invention, which uses the steam generator will be described with reference to FIGS. 21 through 27. In addition, FIG. 21 is a perspective view showing the first embodiment of the mixer in accordance with the present invention. FIG. 22 is a perspective view of the silica glass body as shown in FIG. 21. FIGS. 23 illustrate the heater unit as shown in FIG. 21, FIG. 23A is a view from the heater formation side, and FIG. 23B is a side view. FIG. 24 is a schematic vertical sectional view of the embodiment as shown in FIG. 21. FIG. 25 is a cross-sectional view showing a modification of the mixing portion. FIGS. 26A and 26B are respectively a front view and side view showing a diffusion plate. FIG. 27 is a schematic vertical sectional view of the embodiment as shown in FIG. 21. Like reference numerals are used to refer to like parts in the embodiments of the above-mentioned steam generator, and the detailed description of them will not be repeated herein.

Furthermore, in this embodiment and the embodiments subsequent to this embodiment, a case where a thermal decomposition gas (reduction gas), ammonia, is generated using solid (powder) urea material as the material will be described.

Reference symbol B in FIG. 21 denotes a mixer which comprises the silica glass body 10 and the heater unit 20. In this silica glass body 10, the liquid tank portion 1 which stores water and the evaporator portion 2 which is communicated with the above-mentioned liquid tank portion 1, heats the water supplied from the above-mentioned liquid tank portion 1 and generates steam are formed. Moreover, in the above-mentioned silica glass body 10, the steam storage portion 3 is formed which communicates with the above-mentioned evaporator portion 2, and stores the steam generated by the above-mentioned evaporator portion 2.

Similar to the case of the above-mentioned steam generator A, a transverse sectional area of the above-mentioned evaporator portion 2 is formed smaller than the transverse sectional area of the liquid tank portion 1. Since the above-mentioned evaporator portion 2 is thus formed to have the smaller transverse sectional area, the heating efficiency can be improved and the steam can be generated at an early stage after heating.

As shown in FIG. 27, a side wall 2a of the evaporator portion 2 is made into a slope, and a transverse sectional area spreads or expands gradually from the liquid tank portion 1 side towards a steam storage portion 3 side. As described above, the transverse sectional area of the evaporator portion 2 which is in contact with the liquid tank portion 1 is made to be smaller, so that a convection current of water in the liquid tank portion 1 and of water of the evaporator portion 2 is controlled, to thereby generate the steam more easily and more efficiently.

A side end 3a of the above-mentioned steam storage portion 3 is formed in the shape of a circular arc, so that the steam stored in the steam storage portion 3 may not stagnate and the steam may be introduced into an outlet port 3b formed at the upper surface of the other end of the steam storage portion 3.

This steam storage portion 3 is provided for controlling fluctuations in steam pressure, so as to suppress the fluctuations in steam pressure caused by fluctuations in the amount of water in a water tank 1 and fluctuations in the amount of the generated steam.

Moreover, within the above-mentioned silica glass body 10, a steam supply passage 71 is formed which extends from the above-mentioned steam storage portion 3 to a mixing portion 70. A material supply passage 73 connected with a material heating portion 72 which liquefies the material is connected to the mixing portion 70.

Moreover, a material container portion 74 for containing therein solid urea which is the material is formed at an upper part of the above-mentioned material heating portion 72. A side surface 74a of this material container portion 74 is formed as a taper surface. As a result the solid urea moves downwards gradually. On reaching the material heating portion 72, the solid urea is liquefied and drawn through the above-mentioned material supply passage 73 to the mixing portion 70. Then, in the above-mentioned mixing portion 70, it is mixed with the steam from the steam supply passage 71, so that ammonia which is a thermal decomposition gas (reduction gas) is generated.

Furthermore, with reference to FIG. 24, a connection (mixing portion 70) of the steam supply passage 71 from the steam storage portion 3, and the material supply passage 73 from the above-mentioned material heating portion 72 in the above-mentioned mixing portion 70 will be described.

At the above-mentioned connection, the above-mentioned steam supply passage 71 is connected to the material supply passage 73 at an angle of 0 degree (both are parallel) to 45 degrees. Al this stage, a cross-sectional area of the mixing portion 70 is formed to be larger than the cross-sectional area of the steam supply passage 71.

Therefore, when the steam is derived from the steam supply passage 71, where the cross-sectional area is small, to the mixing portion 70 having the larger cross-sectional area, the liquefied urea is sucked and derived by a negative pressure occurred during the derivation and drawn to the mixing portion 4, and both are mixed When the above-mentioned steam supply passage 71 is formed at an angle which exceeds 45 degrees with respect to the material supply passage 73, the effect of sucking the above-mentioned liquefied urea cannot be acquired. Preferably, the above-mentioned steam supply passage 71 is formed at an angle of not less than 5 degrees and not more than 20 degrees with respect to the material supply passage 73. Moreover, in the case of less than 5 degrees, an upward flow occurs inside the mixing portion 70 and reduces the effect of sucking liquefied urea, this is not preferred. On the other hand, when the angle exceeds 20 degrees, a flow rate of the steam is reduced so that the suction effect is decreased, this is not preferred. More preferably, the angle is in the range of 10 to 30 degrees.

Moreover, the connection between the steam supply passage 71 and the material supply passage 73 may be formed into a double tube structure 35 in which the steam supply passage 5 covers a circumference of the material supply passage 7 as shown in FIG. 25.

In the case of the thus constructed double tube structure 75, the upward flow inside the mixing portion 70 is controlled so that the effect of sucking the liquefied urea is not reduced and mixing urea with the steam is promoted, this is preferable.

Moreover, a passageway 70a for externally deriving the generated ammonia is formed at the mixing portion 70 as shown in FIG. 21. This outlet port 70a is formed so as to spread or expand gradually and outwardly from the mixing portion 70, that is, its vertical section has a shape of trapezoid or trapezium.

As shown in FIG. 26 the diffusion plate 36 for diffusing a thermal decomposition gas is provided in the passageway 70a. This diffusion plate 36 has formed therein through holes 36a through which ammonia passes, and is fixed to a side wall of a passageway 70a by the support portion 36b. Preferably this diffusion plate 36 is formed of the silica glass and fixed to the side wall of the above-mentioned passageway 70a by fusion welding. In this way, homogeneous ammonia can be externally diffused by the diffusion plate 36.

As shown in FIG. 21, this silica glass body 10 is provided with a pipe 5 which supplies water to the above-mentioned liquid tank portion 1 and a channel 10a which connects the pipe 5 and the liquid tank portion 1. The above-mentioned pipe 5 projects from the side surface of the silica glass body 10, and is connected to a water source of supply (not shown). The channel 10a is formed within the silica glass body 10.

Moreover, the thermocouple insertion hole 10b for inserting therein the thermocouple is formed above the outlet port 3b of the above-mentioned steam storage portion 3 and under the taper surface 74a of the above-mentioned material container portion 74. Based on the resulting temperature measurement by means of the thermocouple, a voltage applied to the heater unit 20 (a carbon wire heater body 21) which will be mentioned later is controlled so that the evaporator portion 2 etc. reach and maintain a predetermined temperature.

As shown in FIG. 22, the above mentioned liquid tank portion 1, the evaporator portion 2, the steam storage portion 3, the outlet port 3b, the steam supply passage 71, the mixing portion 70, the passageway 70a, the material container portion 74, the material heating unit 72, the material supply passage 73, and the thermocouple insertion hole 10b are formed as a recess in the silica glass body 10.

As shown in FIG. 21, the opening side of the above-mentioned recess is covered by the heater unit 20 (which will be mentioned later), so as to formed the liquid tank portion 1, the evaporator portion 2, the steam storage portion 3, the outlet port 3b, the steam supply passage 71, the mixing portion 70, the passageway 70a, the material container portion 74, the material heating portion 72, the material supply passage 73, and the thermocouple insertion hole 10b.

Since the structure of the heater unit 20 is the same structure as the heater unit 20 in the above mentioned steam generating apparatus, its detailed description will not be repeated hereafter but its brief description.

As shown in FIG. 21, this heater unit 20 is welded to a side of the silica glass body 10 and constructed so as to close the above-mentioned liquid tank portion 1, the evaporator portion 2, the steam storage portion 3, the outlet port 3b, the steam supply passage 71, the mixing portion 70, the passageway 70a, the material container portion 74, the material heating portion 72, the material supply passage 73, and the recess that forms the thermocouple insertion hole 10b, and to heat the above-mentioned liquid tank portion 1, the evaporator portion 2, the steam storage portion 3, the material heating portion 72, the mixing portion 70, the passageway 70a, the steam supply passage 71, and the material supply passage 73.

The above-mentioned carbon wire heater body 21 is constructed so as to heat the liquid tank portion 1, the evaporator portion 2, the steam storage portion 3, the material heating portion 72, the mixing portion 70, the passageway 70a, the steam supply passage 71, and the material supply passage 73, but different parts need different temperatures. Therefore, the above-mentioned carbon wire heater body 21 is formed densely at a part which needs high temperature, while the above-mentioned carbon wire heater body 21 is formed in sparsely at a part in which a low temperature is sufficient.

For example, when a temperature at the evaporator portion 2 is 100 the carbon wire heater body 21 is arranged to have a formation pattern such that the material heating unit may be heated to 150. to 250. and the mixing portion 4 may be heated 350. to 500.

Moreover, as shown in FIG. 23, the reflection film or the reflection member 19 is formed in the silica glass plate 22 in which the carbon wire heater body 21 of the heater unit 20 is enclosed.

Next, operation of the mixer B will be described.

The solid urea of material is placed in the material container portion 74 in advance. While, a predetermined amount of water is supplied through the pipe 5 and the channel 10a to the liquid tank portion 1. In this state, when electric power is supplied to the carbon wire heater body 21, the liquid tank portion 1 and the evaporator portion 2 are heated so as to generate steam.

Especially, since the transverse sectional area of the evaporator portion 2 is smaller than that of the liquid tank portion 1, the steam can be generated efficiently in the evaporator portion 2.

The thus generated steam is stored in the steam storage portion 3 temporarily, and then supplied through the outlet port 3b and the steam supply passage 71 to the mixing portion 70. At this stage, the above-mentioned carbon wire heater body 21 heats the steam storage portion 3, the outlet port 3b, and the steam supply passage 71 so that steam condensation can be inhibited.

On the other hand, the solid urea placed in the material heating portion 74 is heated to about 160. melted and liquefied by the carbon wire heater body 21, and temporarily stored in the material heating portion 72 which is located under the material container portion 74. Then, it is supplied to the mixing portion 70 through the above-mentioned material feed portion 72. The liquefied urea and the above-mentioned steam are mixed in this mixing portion 70. Since the mixing portion 70 is heated to 350. to 500. by the carbon wire heater body 21, the urea is thermally decomposed to generate ammonia and carbon dioxide.

That is, $(NH_2)_2CO + H_2O \rightarrow 2NH_3 + CO_2$

The generated ammonia and carbon dioxide are derived through the passageway 70a.

The derived ammonia is supplied to a reducing agent feed nozzle 154 arranged at the exhaust pipe 153 as described in the conventional example, and to $NO_x$ reduction catalyst 101 arranged in the middle of the exhaust pipe of a diesel engine, decomposes $NO_x$ into nitrogen and water and purifies the exhaust gas.

That is, $NO_x + NH_3 \rightarrow N_2 + H_2O$

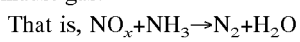

Next, a method of manufacturing the mixer B will be described.

The method of manufacturing the mixer B is similar to that of the steam generating apparatus. Firstly, in the silica glass body 10, a recess is formed to be the liquid tank portion 1, the evaporator portion 2, the steam storage portion 3, the outlet port 3b, the steam supply passage 71, the mixing portion 70, the material heating portion 72, the material container portion 74, the material supply passage 73, and the passageway 70a. Moreover, the channel 10a connected to the liquid tank portion 1 and the pipe 5 connected to the channel 10a are formed in the above-mentioned silica glass body 10. The thermocouple insertion hole 10b is formed which inserts therein a thermocouple.

On the other hand, the slot 22a which contains therein the carbon wire heater body 21 is formed in the silica glass plate 22, and the above-mentioned carbon wire heater body 21 is placed at the above-mentioned slot 22a.

Then, a mirror finishing process is carried out for the slot formation side (surface where the carbon wire heater body 21 is provided) of the above-mentioned silica glass plate 22, and for the surface of the silica glass plate 23 (the surface being opposite to or facing the surface of the slot formation side of the silica glass plate 22). Another mirror finishing process is carried out for a surface on the recess formation side of the glass body 10 and for the surface of the silica glass plate 23 (the surface being opposite to or facing the surface on the recess formation side of the glass body 10).

Then, similar to the case as shown in FIG. 11, the three members are stacked and are placed in the high temperature processing furnace so that adhesion surfaces may be horizontal. The three members are welded and unified by applying the load of 0.1 kgf/cm$^2$ to them at 1450.

After fusion welding, the end of the carbon wire heater body 21 is arranged to be located among three uniform wire carbon bundles (the wire carbon member 27) and substantially in the center of the above-mentioned quartz glass tube 26. Then, the above-mentioned silica glass tube 26 is accommodated in the silica glass tube 29 and the above-mentioned silica glass tube 29 is welded and fixed to the back of the silica glass plate 21

Moreover, similar to the cases as shown in FIG. 6 and FIG. 7, one end of the inner side connection line 28 is inserted into the wire carbon bundles (wire carbon member 27), and the other end is fixed to one end of the Mo foil 30. Two outer connection lines 25 are fixed to the other end of the Mo foil 30. Under a nitrogen atmosphere, the end of the silica glass tube 29 is subjected to the pinch seal and hermetically sealed at a pressure of 100 torr inside the silica glass tube 29.

Finally, the thermocouple is inserted into the thermocouple insertion hole 10b so as to complete the mixer.

Next, an experiment for confirmation was conducted using the mixer B.

Firstly, powder (solid) urea was inputted into the material container portion 74 up to its upper end. Further, water was fed into the liquid tank portion 1 and the evaporator portion 2 up to the middle level of each of them. The outer connection lines 25 of the carbon wire heater body 21 were connected with a voltage regulator (A/C power supply), and were supplied with electric power at an alternating voltage of 0 to 130V.

At this time, the resistance of the carbon heater unit 20 before supplying the electric power was 33. While measuring a temperature by means of the thermocouple, the temperature at the evaporator portion 2 was adjusted to be 100. At this time the material heating unit was heated to 160, and the solid urea was liquefied.

After being stored in the steam storage portion 3, the generated steam was supplied to the mixing portion 70 and mixed with the liquefied urea. A temperature of the gas derived through the passageway 70a formed at an end of the mixing portion 70 was 450. Moreover, ammonia was identified as being generated.

As described above, in the mixer in accordance with the above embodiment, the solid urea is heated to be liquefied and mixed with the steam. In addition, since the solid urea is heated also in the mixing portion, it is not necessary to rapidly heat the solid urea inside the flue, and the heater can be miniaturized, unlike the conventional way.

Moreover, in the mixer in accordance with the above embodiment, the steam is used as a means for generating and conveying ammonia. In addition, since the water tank which stores the water for generating steam is provided in the silica glass body, not only the air feed unit is unnecessary but also the whole apparatus can be minimized as compared with the conventional one.

Furthermore, since the steam is maintained in a heating state, it is possible to prevent the thermal efficiency from decreasing due to the fall in the temperature in the flue because of the air supply, unlike the conventional one.

Still further, in the mixer in accordance with the above embodiment, since the liquid tank portion, the evaporator portion, the steam storage portion, the material heating unit, the mixing portion, etc. are formed in the silica glass body, it is not necessary to connect respective portions by means of piping etc., thus the whole apparatus can be miniaturized.

In addition, the mixer in accordance with the above embodiment comprises the silica glass body and the heater unit enclosed in the silica glass plate, so that the flue etc. are not corroded by ammonia, thus being, unnecessary to employ a Teflon(registered trademark) coating.

Figure 28A:
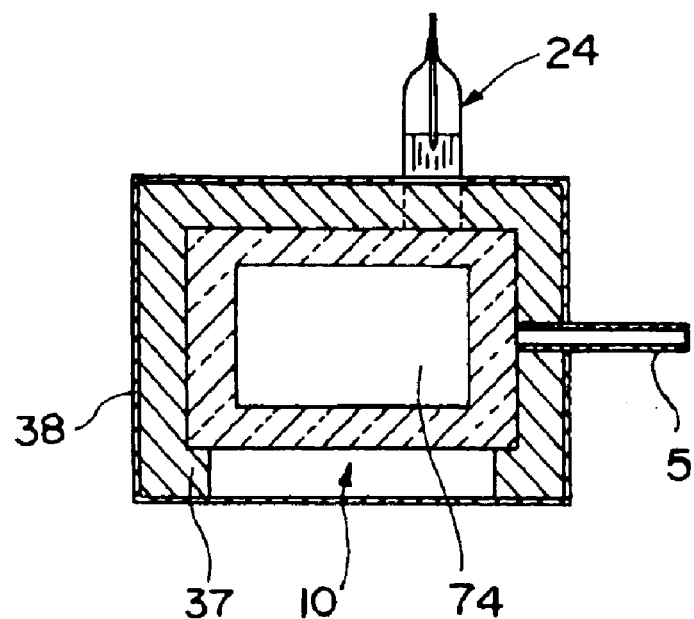
FIGS. 28A and 28B show a second embodiment of the mixer in accordance with the present invention, FIG. 2BA is a cross-sectional view along the line I—I in FIG. 28B.
Figure 28B:
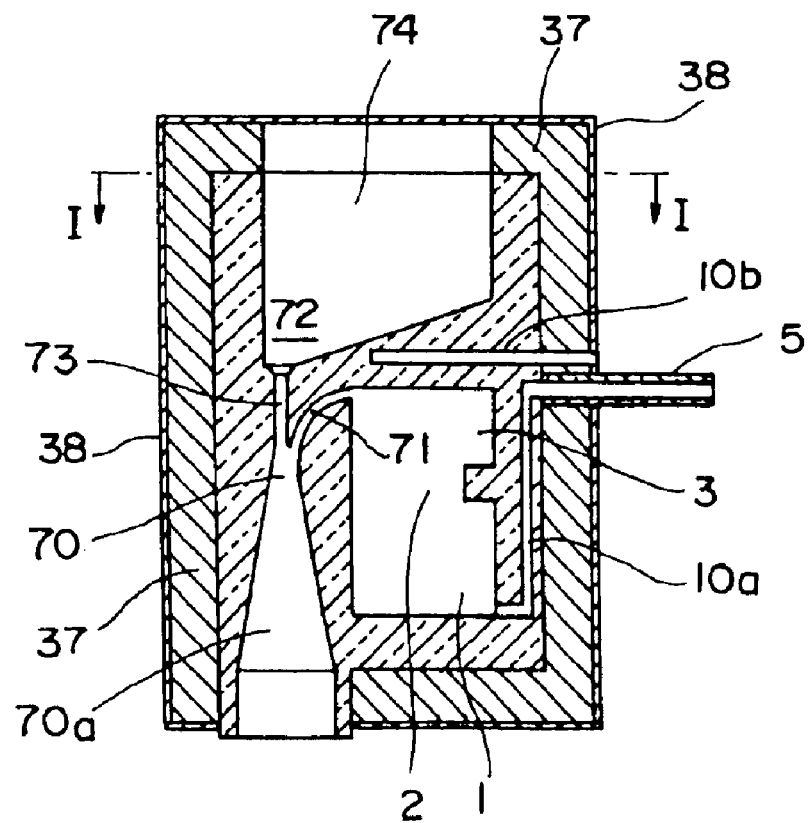

Next, a second embodiment of the mixer in accordance with the present invention will be described with reference to FIGS. 28. In addition, FIGS. 2B and 28B show a state where the mixer is accommodated in the metal casing together with the thermal insulation material, FIG. 28A is a cross-sectional view along the line I—I in FIG. 28B, and FIG. 28B is a vertical sectional view.

In this embodiment, the above-mentioned mixer of the first embodiment is surrounded by the thermal insulation material 37.

In other words, the silica glass body 10 and the heater unit 20 are surrounded by the thermal insulation material 37, such as glass wool, a fiber flux board, and a porous-ceramics block, rock wool, etc., and are further accommodated in the metal casing 38.

Since the silica glass body 10 and the heater unit 20 are thus surrounded by the thermal insulation material 37, the heating can be performed efficiently. Further, being accommodated in the metal casing 38, the mixer can be protected from an impact etc., therefore suitably mounted on a vehicle.

In addition, when the thermal insulation material 37 is glass wool etc., it functions as a so-called shock absorbing material, thus protecting the mixer against the impact etc.

Next, a third embodiment of the mixer in accordance With the present invention will be described with reference to FIG. 29 and FIG. 30. In addition, FIG. 29 is a schematic vertical sectional view showing the third embodiment of the present invention, FIG. 30 is a schematic vertical sectional view showing a modification of the third embodiment which showed in FIG. 29.

This embodiment is characterized by being provided with the porous body 40 at the above-mentioned evaporator portion 2 and in the liquid tank portion 1.

Figure 29:
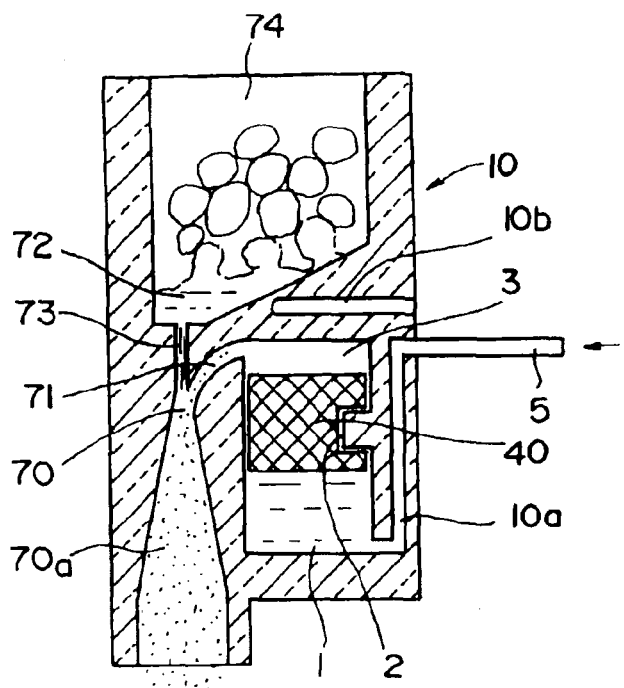
FIG. 29 is a schematic vertical sectional view showing a third embodiment of the mixer in accordance with the present invention.
Figure 30:
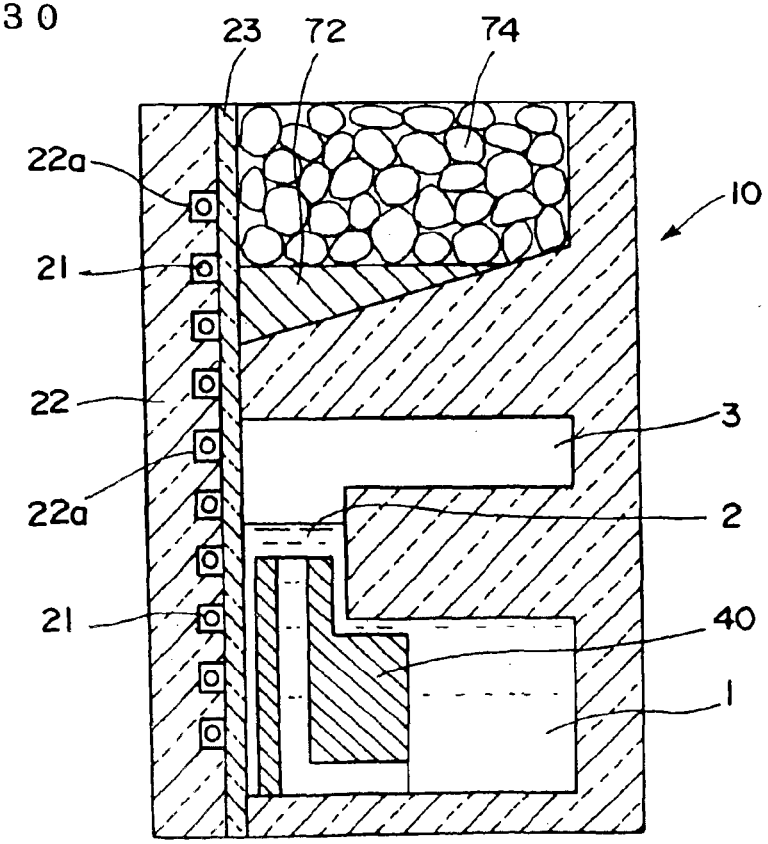
FIG. 30 is a schematic vertical sectional view showing a modification of the third embodiment as shown in FIG. 29.

In other words, as shown in FIG. 29, when the porous body 40 is provided at the above-mentioned evaporator portion 2 and in the liquid tank portion 1, the water supply to the evaporator portion 2 is stabilized by capillary phenomena in the porous body 40. Moreover, bumping in the evaporator portion 2 and the liquid tank portion 1 can be prevented. In addition, although a lower end part of the porous body 40 is located at an upper part of the water tank 1 in FIG. 29, the lower end part of the porous body 40 may be located at a lower part (bottom) of the liquid tank portion 1.

Moreover, as for the porous body 40, porous silica glass, porous SiC, a carbon porous body, carbon felt, a porous brick, and glass wool yarn can be used. However, when the porous SiC, the carbon porous body, etc. are used as the porous body 40, it is preferable that the whole porous body 40 is provided in the water, in order to prevent the porous body 40 from being oxidized in contact with the steam.

As shown in FIG. 30, when the porous body 40 is formed of a material having a heat capacity to some extent (endothermic body) such as an SiC material, a carbon material, etc. and the porous body 40 is provided at the above-mentioned evaporator portion 2 and in the liquid tank portion 1, it is possible to store the heat from the heater unit 20 and improve the heat transfer efficiency with respect to water.

The porous body 40 in this case may only have a certain heat capacity, and its material is not particularly limited in this regard. However, the porous body 40 is preferably provided in the water, in order to prevent the porous body 40 from being oxidized in contact with the steam when a carbon fiber etc. is used as the porous body 40. Moreover, the pores in the porous body 40 increase the touch area in contact with water, to thereby improve the steam generating efficiency.

Figure 31:
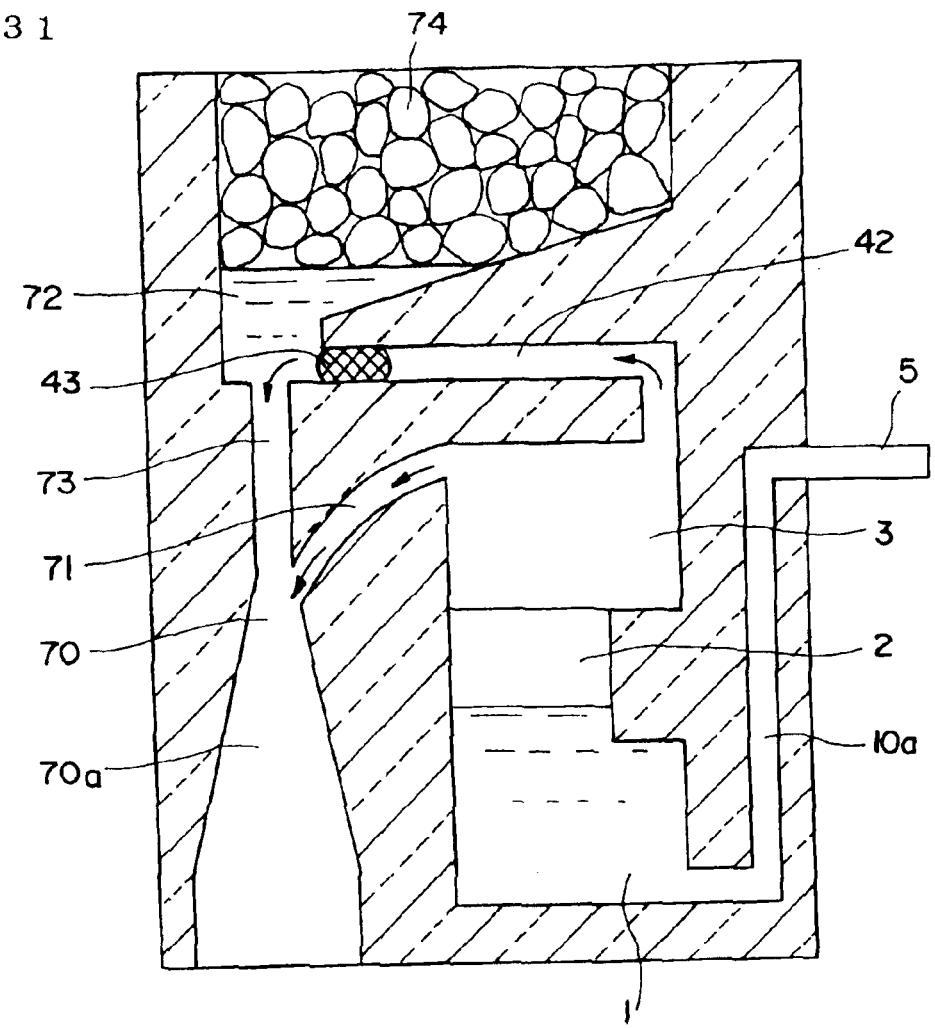
FIG. 31 is a schematic vertical sectional view showing a fourth embodiment of the mixer in accordance with the present invention.

Next, a fourth embodiment of the mixer in accordance with the present invention will be described with reference to FIG. 31. In addition, FIG. 31 is a schematic vertical sectional view showing the fourth embodiment.

This embodiment is characterized by forming the steam supply passage 42 extending from the steam storage portion 3 to the material heating portion 72 and by arranging the porous body 43 in the above-mentioned steam supply passage 42.

As described in the first embodiment already, the solid urea is heated and liquefied in the material heating portion 72, and supplied to the mixing portion 70. However, since the viscosity of the above-mentioned liquid urea is high, there is a possibility that a smooth flow may not be obtained.

In this embodiment, part of the steam stored in the steam storage portion 3 is supplied to the material heating portion 72, so that the viscosity of liquefied urea is reduced, the fluidity is improved, and the above-mentioned disadvantages are removed.

As described above, part of the steam stored in the steam storage portion 3 is fed to the material heating portion 72, the viscosity of the liquefied urea is reduced, and the fluidity is improved, so that the dispersibility of the urea in the mixing portion 70 is promoted, and mixing with steam is promoted.

Further, as described above, the porous body 43 is arranged in the steam supply passage 42, the liquefied urea can be prevented from entering the steam supply passage 42.

Moreover, it is possible to improve an effect of dispersing the steam into the liquefied urea by means of the material heating unit 72, and the liquefied urea can be caused to have a uniform viscosity.

Figure 32:
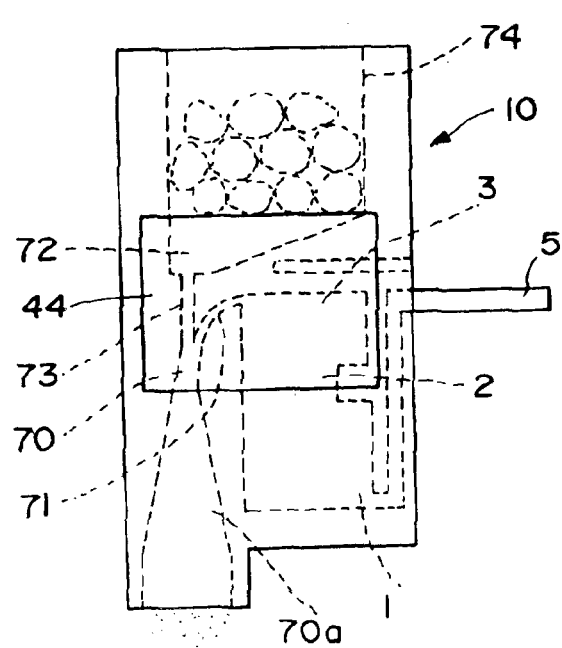
FIG. 32 is a schematic side view showing a fifth embodiment of the mixer in accordance with the present invention.

Next, a fifth embodiment of the mixer in accordance with the present invention will be described with reference to FIG. 32. In addition, FIG. 32 is a schematic side view showing the fifth embodiment.

This embodiment is characterized in that the heat equalizing plate 44 or the heat equalizing coating which equalizes the heat conduction from the above-mentioned heater unit to each part of the above-mentioned silica glass body 10 is formed between the heater unit 20 and the silica glass body 10.

In this way, between the above-mentioned heater unit and the above-mentioned silica glass body, the heat equalizing plate or the heat equalizing coating 44 is provided particularly in the side position of the evaporator portion 2, the steam storage portion 3, the steam supply passage 71, the material heating portion 72, the material supply passage 73, and the mixing portion 70 of the above-mentioned silica glass body 10, so that the temperature at each of the above-mentioned parts can be equalized and the thermal efficiency can be improved.

In addition, the above-mentioned heat equalizing plate 44 and the heat equalizing coating 44 may employ the same materials as those for the above-mentioned steam generating apparatus.

The embodiments as shown in FIGS. 16 through 20 with respect to the above-mentioned steam generating apparatus may similarly apply to this mixer.

Figure 33A:
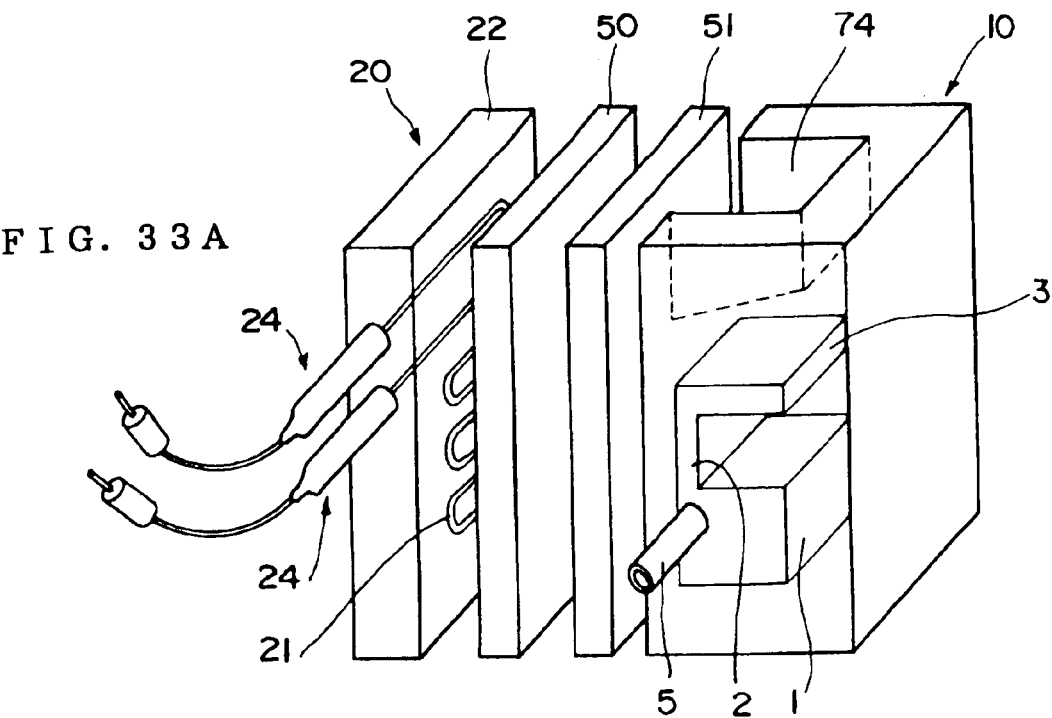
FIGS. 33A and 33B are schematic perspective views showing other embodiments in accordance with the present invention.
Figure 33B:
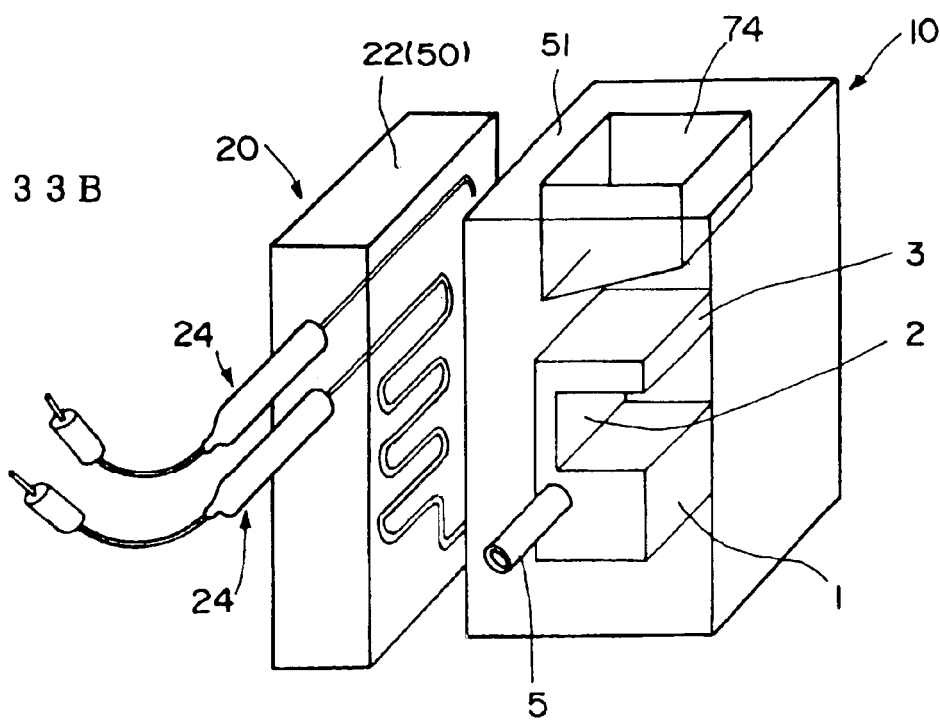
Figure 34:
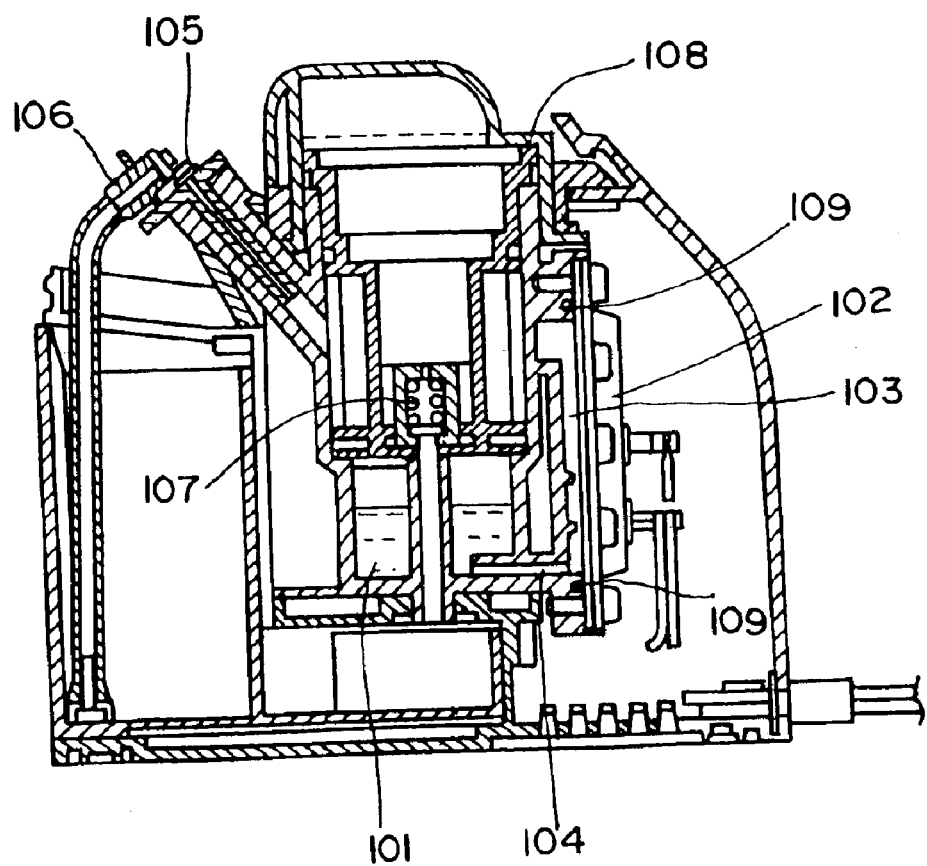
FIG. 34 is a schematic structural view showing a conventional steam generator (a steam suction apparatus).
Figure 35:
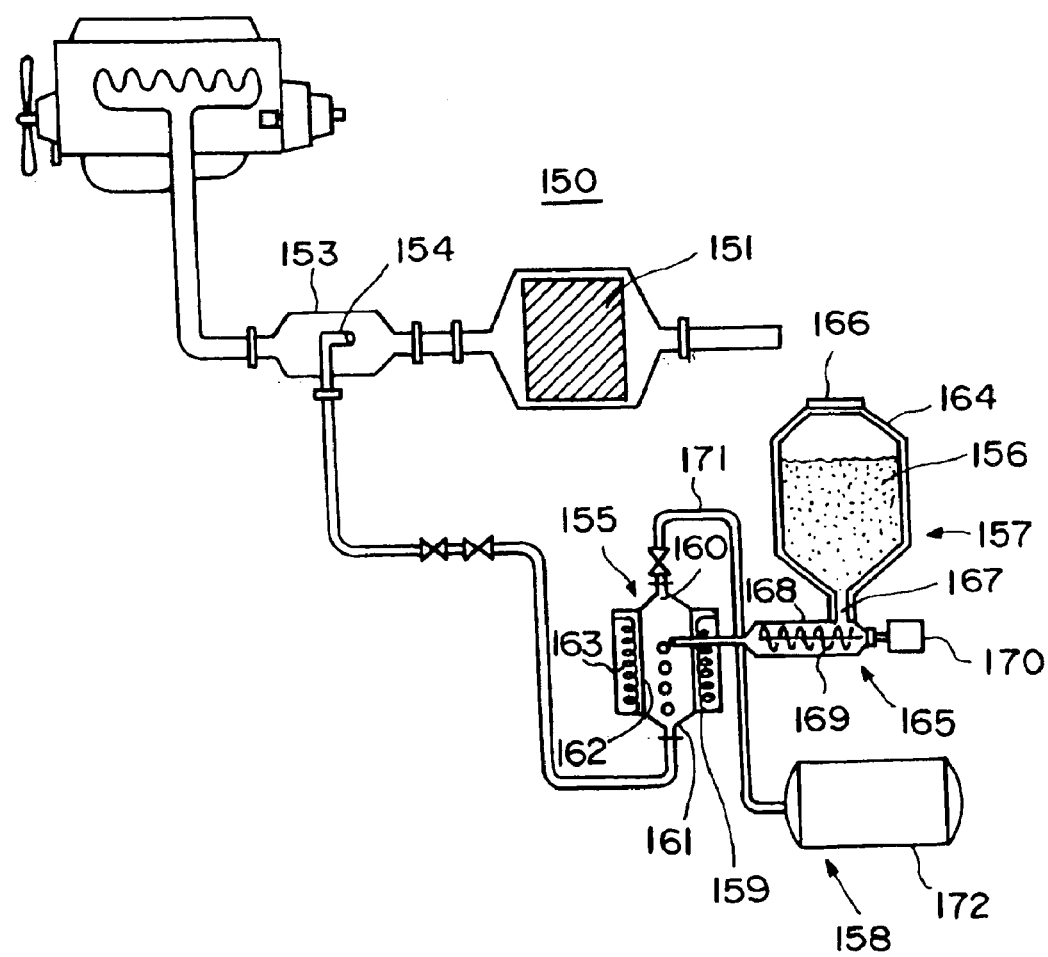
FIG. 35 is a schematic structural view showing a conventional exhaust gas purification apparatus.

For example, as shown in FIG. 33, the silica glass body 10 and the heater unit 20 may not be integrated by fusion welding but formed to be separable.

In other words, as shown in FIG. 33A, the above-mentioned carbon wire heater body 21 is placed at the slot 22a of the silica glass plate 22, to which the silica glass plate 50 is welded, so as to form the heater unit 20.

On the other hand, the liquid tank portion 1, the evaporator portion 2, the steam storage portion 3, the outlet port 3b, the steam supply passage 71, the mixing portion 70, the passageway 70a, the material container portion 74, the material heating portion 72, the material supply passage 73, and the thermocouple insertion hole 10b are formed in the silica glass body 10 as the recess. The silica glass plate 51 is welded to the recess side surface of the silica glass body 1.

Then, the above-mentioned heater unit 20 and the silica glass body 10 are separately formed as shown in FIG. 20B.

As to the heater unit 20 and the silica glass body 10, the silica glass body 10 and the heater unit 20 are surrounded by the thermal insulation material 37 as shown in FIG. 28, and are accommodated in the metal casing 38 further.

As described above, since the heater unit 20 and the silica glass body 10 are formed separately, when breakage etc. occur, the breakage may be easily repaired by only replacing them. Moreover, when the urea which is an organic substance adheres to the inside of the silica glass body 10 and is charred, the silica glass body 10 may only be 800. or more in the air so as to evaporate or oxidize the charred substance, whereby the silica glass body 10 can be cleaned easily.

According to the present invention, the mixer can be provided which is small, has a good efficiency, can generate the mixed gas efficiently, and has an excellent resistance corrosion.

What is claimed is:

1. A steam generator comprising:
    a liquid tank portion for storing a liquid;
    an evaporator portion which is directly connected to said liquid tank portion, heats the liquid supplied from said liquid tank portion, and generates steam;
    a steam storage portion which is directly connected to said evaporator portion, and stores the steam generated by said evaporator portion;
    a passageway which is directly connected to said steam storage portion and outwardly passes the steam generated by said evaporator portion;
    a liquid pathway which is connected to said liquid tank portion, and supplies the liquid to said liquid tank portion; and
    a heater unit which is provided at one side of said evaporator portion and at least heats the evaporator portion, wherein said liquid tank portion, the evaporator portion, the steam storage portion, the passageway, and the liquid pathway are formed within an integral member of a translucent material,
    wherein said integral member of said translucent material is any one of a transparent silica glass body, a transparent borosilicate glass body, and a transparent soda glass body.
2. The steam generator as claimed in claim 1, wherein a transverse sectional area of said evaporator portion is smaller than that of the liquid tank portion, and formed such that the transverse sectional area may gradually spread or expand from the liquid tank portion side towards the steam storage portion side.

3. The steam generator as claimed in claim 2, wherein a porous body is provided at said evaporator portion and in the liquid tank portion.

4. The steam generator as claimed in claim 3, wherein a vertical section of said passageway is formed into a trapezoid or a trapezium where the section spreads or extends gradually outwards, and a diffusion plate is provided within said passageway.

5. The steam generator as claimed in claim 1, wherein said heater unit is a heater in which a carbon wire heater body is enclosed in a glass plate.

6. The steam generator as claimed in claim 5, wherein said heater unit welds together a first glass plate in which a slot for accommodating the carbon wire heater body is formed and a second glass plate for covering said slot, to thereby enclose the carbon wire heater body in the glass plate.

7. The steam generator as claimed in claim 5, wherein said integral member of said translucent material at which at least said liquid tank portion, the evaporator portion, the steam storage portion, and the passageway are formed and the heater unit provided on the side of said integral member of said translucent material are surrounded by a thermal insulation material and accommodated in a metal casing.

8. The steam generator as claimed in claim 1, wherein said liquid tank portion, the evaporator portion, the steam storage portion, and the passageway are formed as a recess at said glass body, the opening side of said recess is covered by the heater unit in which the carbon wire heater body is enclosed in a glass plate, and the glass plate of said heater unit is welded to the side of said glass body so as to integrate said glass body with the heater unit, whereby the liquid tank portion, the evaporator portion, the steam storage portion, and the passageway are formed.

9. A mixer using a steam generator comprising:

a liquid tank portion for storing a liquid;

an evaporator portion which is directly connected to said liquid tank portion, heats the liquid supplied from said liquid tank portion, and generates steam;

a steam storage portion which is directly connected to said evaporator portion, and stores the steam generated by said evaporator portion; and a liquid pathway which is connected to said liquid tank portion, and supplies the liquid to said liquid tank portion, wherein said liquid tank portion, the evaporator portion, the steam storage portion, and the liquid pathway are formed in a silica glass body, wherein a material beating portion for heating a material;

a mixing portion for mixing the steam from said steam storage portion and the material so as to generate a mixed gas; and a passageway which passes said mixed gas outside are formed, and a heater unit for heating said evaporator portion and the material heating portion is provided on a side of said silica glass body.

10. The mixer as claimed in claim 9, wherein the liquid tank for storing water as said liquid and the steam storage portion which is communicated with said evaporator portion and stores the steam generated by said evaporator portion are provided; and the steam from said steam storage portion and the material are mixed in said mixing portion so as to generate the mixed gas.

11. The mixer as claimed in claim 10, wherein at an interconnection between the steam supply passage extending from said steam storage portion to the mixing portion and the material supply passage extending from said material heating portion to the mixing portion, said steam supply passage is connected to the material supply passage at an angle of 0 to 45 degrees therebetween.

12. The mixer as claimed in claim 11, wherein the interconnection between the steam supply passage extending from said steam storage portion to the mixing portion and the material supply passage extending from said material heating portion to the mixing portion is formed into a double tube structure in which said steam supply passage covers a periphery of the material supply passage.

13. The mixer as claimed in claim 9, wherein the steam storage portion which is communicated with said evaporator portion and stores the steam generated by said evaporator portion, a steam supply passage extending from said steam storage portion to the mixing portion, and a steam supply passage extending from said steam storage portion to the material heating portion are provided; and the steam is supplied to said material heating portion, and the steam from said steam storage portion and the material are mixed in said mixing portion, so as to generate the mixed gas.

14. The mixer as claimed in claim 13, wherein a porous body is disposed within the steam supply passage extending from said steam storage portion to the material heating portion.

15. The mixer as claimed in claim 9, wherein a material container portion for containing the material is provided within said silica glass body, and the material heating portion for heating the material is provided at the lower part of said material container portion.

16. The mixer as claimed in claim 9, wherein said heater unit is a heater in which the carbon wire heater body is enclosed in the silica glass plate, the liquid tank portion, the evaporator portion, the steam storage portion, the material heating portion, the mixing portion, and the passageway are formed as the recess at the silica glass body, the opening side of said recess is covered by welding the silica glass plate of said heater unit to said silica glass body, whereby, a water tank portion, the evaporator portion, the steam storage portion, the material container portion, the material heating portion, the mixing portion, and the passageway are formed.

17. The mixer as claimed in claim 16, wherein the carbon wire heater body of said heater unit is arranged to be located at sides of at least said evaporator portion, the steam storage portion, and the material heating portion.

18. The mixer as claimed in claim 9, wherein the silica glass body at which at least said liquid tank portion, the evaporator portion, the material heating portion, the mixing portion, and the passageway are formed and the heater unit provided at a side of said silica glass body are surrounded by a thermal insulation material and accommodated in a metal casing.

19. The mixer as claimed in claim 18, wherein said material is solid urea and said mixed gas is a gas containing ammonia which is a thermal decomposition gas.

* * * * *